(12) United States Patent
Gao et al.

(10) Patent No.: US 9,408,921 B2
(45) Date of Patent: Aug. 9, 2016

(54) ANTINEOPLASTIC HYDROGELS, AND ENZYME-INSTRUCTED PREPARATIONS THEREOF

(71) Applicant: Brandeis University, Waltham, MA (US)

(72) Inventors: Yuan Gao, Waltham, MA (US); Yi Kuang, Waltham, MA (US); Bing Xu, Newton, MA (US)

(73) Assignee: Brandels University, Waltham, MA (US)

( * ) Notice: Subject to any disclaimer, the term of this patent is extended or adjusted under 35 U.S.C. 154(b) by 0 days.

(21) Appl. No.: 14/189,185

(22) Filed: Feb. 25, 2014

(65) Prior Publication Data
US 2014/0235550 A1  Aug. 21, 2014

Related U.S. Application Data

(63) Continuation of application No. 13/379,801, filed as application No. PCT/US2010/039789 on Jun. 24, 2010, now Pat. No. 8,658,600.

(60) Provisional application No. 61/220,657, filed on Jun. 26, 2009.

(51) Int. Cl.
| | |
|---|---|
| *A61K 47/48* | (2006.01) |
| *C07D 305/14* | (2006.01) |
| *C07F 9/12* | (2006.01) |
| *C07F 9/655* | (2006.01) |
| *C07K 5/107* | (2006.01) |

(52) U.S. Cl.
CPC ........ *A61K 47/48246* (2013.01); *C07D 305/14* (2013.01); *C07F 9/12* (2013.01); *C07F 9/6552* (2013.01); *C07F 9/65512* (2013.01); *C07K 5/1016* (2013.01)

(58) Field of Classification Search
CPC .. A61K 47/48246; C07D 305/14; C07F 9/12; C07F 9/65512; C07F 9/6552; C07K 5/1016
See application file for complete search history.

(56) References Cited

U.S. PATENT DOCUMENTS

| | | | |
|---|---|---|---|
| 6,271,384 B1 | 8/2001 | Nicolaou et al. | |
| 6,576,679 B2 | 6/2003 | Kimizuka et al. | |
| 2008/0193968 A1* | 8/2008 | Xu et al. | 435/41 |

FOREIGN PATENT DOCUMENTS

| | | |
|---|---|---|
| JP | 200285957 | 3/2002 |
| WO | 9518613 A1 | 7/1995 |

OTHER PUBLICATIONS

International Search Report dated Mar. 28, 2011, from PCT/US2010/039789.
Branco et al., "Self-assembling Materials for Therapeutic Delivery," Acta Biomaterilia, 5(3):817-831 (2009).
de Loos et al., "Design and Application of Self-Assembled Low Molecular Weight Hydrogels," European Journal of Organic Chemistry, 2005(17):3615-3631 (2005).
Estroff et al., "Water Gelation by Small Organic Molecules," Chemical Review, 104(3):1201-1218 (2004).
Zhang et al., "Supramolecular Hydrogels Respond to Ligand-receptor Interaction," J. Am. Chem. Soc., 125 (45):13680-13681 (2003).

* cited by examiner

*Primary Examiner* — James D Anderson
(74) *Attorney, Agent, or Firm* — LeClairRyan, a Professional Corporation

(57) ABSTRACT

Disclosed is a general methodology to create nanofibers of therapeutic molecules that have a dual role, as both the delivery vehicle and the drug itself. It is shown that with proper molecular design, the integration of enzymatic reaction and self-assembly provides a powerful method to create molecular hydrogels of clinically-used therapeutics without compromising their bioactivities. In addition, the results disclosed herein demonstrate enzyme-instructed self-assembly as a facile strategy for generating the supramolecular hydrogels of molecules that inherently have poor solubility in water. For example, by covalently connecting paclitaxel with a motif that is prone to self-assemble, a hydrogel of paclitaxel can be formed without compromising the activity of the paclitaxel.

16 Claims, 6 Drawing Sheets

(a) succinic anhydride, DIEA, chloroform; (b) NHS, DCC, chloroform; (c) sodium carbonate, acetone, water.

ANTINEOPLASTIC HYDROGELS, AND ENZYME-INSTRUCTED PREPARATIONS THEREOF

RELATED APPLICATIONS

This application is a continuation of U.S. patent application Ser. No. 13/379,801, now U.S. Pat. No. 8,658,600, which is the U.S. National Stage of International Patent Application No. PCT/US10/039789, filed Jun. 24, 2010, which claims the benefit of priority to U.S. Provisional Patent Application Ser. No. 61/220,657, filed Jun. 26, 2009.

GOVERNMENT SUPPORT

This invention was made with government support under Grant No. DMR 0820492 awarded by the National Science Foundation. The government has certain rights in the invention.

BACKGROUND

The majority of hydrogels are polymeric with networks consisting of covalently crosslinked natural or synthetic polymers. Against this backdrop, supramolecular hydrogels, whose networks consist of nanofibers formed through self-assembly of small molecules (i.e., hydrogelators), have emerged as promising biomaterials in the past decade. Estroff, L. A.; Hamilton, A. D. *Chem. Rev.* 2004, 104, 1201; Terech, P.; Weiss, R. G. *Chem. Rev.* 1997, 97, 3133; Kiyonaka, S.; Sada, K.; Yoshimura, I.; Shinkai, S.; Kato, N.; Hamachi, I. *Nat. Mater.* 2004, 3, 58; Xing, B. G.; Yu, C. W.; Chow, K. H.; Ho, P. L.; Fu, D. G.; Xu, B. *J. Am. Chem. Soc.* 2002, 124, 14846; Schneider, J. P.; Pochan, D. J.; Ozbas, B.; Rajagopal, K.; Pakstis, L.; Kretsinger, J. *J. Am. Chem. Soc.* 2002, 124, 15030; Schnepp, Z. A. C.; Gonzalez-McQuire, R.; Mann, S. *Adv. Mater.* 2006, 18, 1869; Silva, G. A.; Czeisler, C.; Niece, K. L.; Beniash, E.; Harrington, D. A.; Kessler, J. A.; Stupp, S. I. *Science* 2004, 303, 1352; and Chen, J.; McNeil, A. J. *J. Am. Chem. Soc.* 2008, 130, 16496. Usually, the change of temperature, pH, or ionic strength can successfully trigger the formation of supramolecular hydrogels. It is, however, more advantageous to use inherent biological processes to create supramolecular hydrogels in vivo or in situ for certain biomedical applications. Hu, B. H.; Messersmith, P. B. *J. Am. Chem. Soc.* 2003, 125, 14298; Yang, Z. M.; Liang, G. L.; Guo, Z. F.; Guo, Z. H.; Xu, B. *Angew. Chem. Intl. Ed.* 2007, 46, 8216. By mimicking biomacromolecular self-assembly (e.g., formation of collagen fibrils), the integration of enzymatic reactions with self-assembly of small molecules provides a effective means to form nanofiber network and result in hydrogels under various conditions. Leikina, E.; Mertts, M. V.; Kuznetsova, N.; Leikin, S. *Proc. Natl. Acad. Sci., USA* 2002, 99, 1314; Toledano, S.; Williams, R. J.; Jayawarna, V.; Ulijn, R. V. *J. Am. Chem. Soc.* 2006, 128, 1070; Williams, R. J.; Smith, A. M.; Collins, R.; Hodson, N.; Das, A. K.; Ulijn, R. V. *Nat. Nanotech.* 2009, 4, 19; Yang, Z.; Liang, G.; Xu, B. *Acc. Chem. Res.* 2008, 41, 315; and Yang, Z. M.; Gu, H. W.; Fu, D. G.; Gao, P.; Lam, J. K.; Xu, B. *Adv. Mater.* 2004, 16, 1440.

While it is feasible to initiate hydrogelation using an enzyme that converts a precursor into a hydrogelator, most precursors explored so far bear limited biological activities. However, it was recently discovered that the enzyme-triggered formation of molecular nanofibers can inhibit bacteria growth or selectively kill cancer cells in vitro; the mechanisms of these phenomena likely differ significantly from that of well-established antineoplastic agents that mainly exploit high affinity ligand-receptor binding.

SUMMARY

One aspect of the invention relates to the synthesis and use of molecular nanofibers as anticancer nanomedicines. In certain embodiments, the invention relates to nanofibers based on enzyme-triggered self-assembly of small molecules. While conventional drug delivery systems require a polymer matrix, and the degradation of the polymer matrix usually cause side effects, the molecular nanofibers disclosed herein allow for self-delivery; that is, because the self-assembled drug molecules form their own gel they eliminate the need for a polymer matrix. In certain embodiments, the self-assembled drug molecules, or the precursors thereto, are represented by formula I:

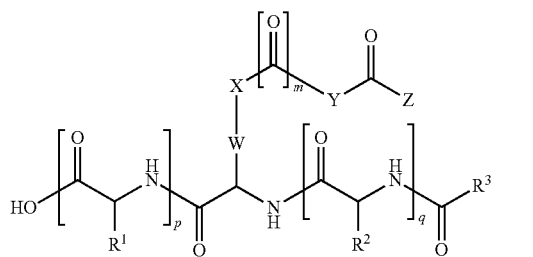

wherein, independently for each occurrence, $R^1$ is

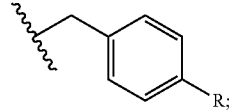

R is —H or —$OPO_3H_2$; p is 0-8; $R^2$ is

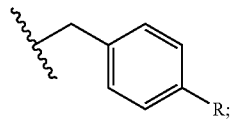

q is 0-8; $R^3$ is aryl, aralkyl, heteroaryl, or heteroaralkyl; W is ($C_1$-$C_{10}$)alkylene; X is —O—, —N(H)—, —S— or —$CH_2$—; m is 0 or 1; Y is ($C_1$-$C_{10}$)alkylene; and Z is bioactive small molecule; provided that the sum of p and q is 2, 3, 4, 5, 6, 7 or 8; and at least one instance of R is —$OPO_3H_2$.

DETAILED DESCRIPTION

Overview

One aspect of the invention relates to the synthesis and use of molecular nanofibers as a anticancer nanomedicines. While conventional drug delivery systems require a polymer matrix, and the degradation of the polymer matrix usually cause side effects, the molecular nanofibers disclosed herein allow for self-delivery; that is, because the self-assembled drug molecules form their own gel they eliminate the need for a polymer matrix.

In certain embodiments the invention relates to the use of an enzymatic reaction to initiate the self-assembly of a derivative of a pharmaceutical agent to form nanofibers that result in a supramolecular hydrogel. Enzymes, as a class of highly efficient and specific catalysts, dictate a myriad of reactions that constitute various cascades in biological systems. The expression and distribution of enzymes differ by the types and states of cells, tissues, and organs, thus leading to diverse extracellular and intracellular environments. Using an enzymatic reaction to convert pharmaceutical agent-containing precursors into amphiphilic molecules (referred to herein as gelators) that self-assemble into nanofibers in water, one can control the cellular responses to molecular nanofiber according to a specific biological condition or environment, thus providing an accessible route to create sophisticated nanomaterials for biomedicine.

In certain embodiments the pharmaceutical agent-containing precursor comprises an antineoplastic agent such as paclitaxel. Paclitaxel is a well-established antineoplastic agent that binds specifically to the β-tubulin subunit of microtubules (MT) to arrest mitosis and result in programmed cell death (i.e., apoptosis) and has shown remarkable activity in the treatment of breast, lung, ovarian, bladder and head and neck cancers. While the invention will often be described herein with paclitaxel as the pharmaceutical agent, this is not intended in any way to limit the scope of the invention to paclitaxel. Rather, other aspects of the invention relate to the self-assembly of derivatives of other neoplastic agents, such as doxorubicin, daunorubicin, vinblastine, or vincristine, as well as other biologically active compounds, such as hydrophobic drugs, to form nanofibers that result in a supramolecular hydrogel.

Figure 1:
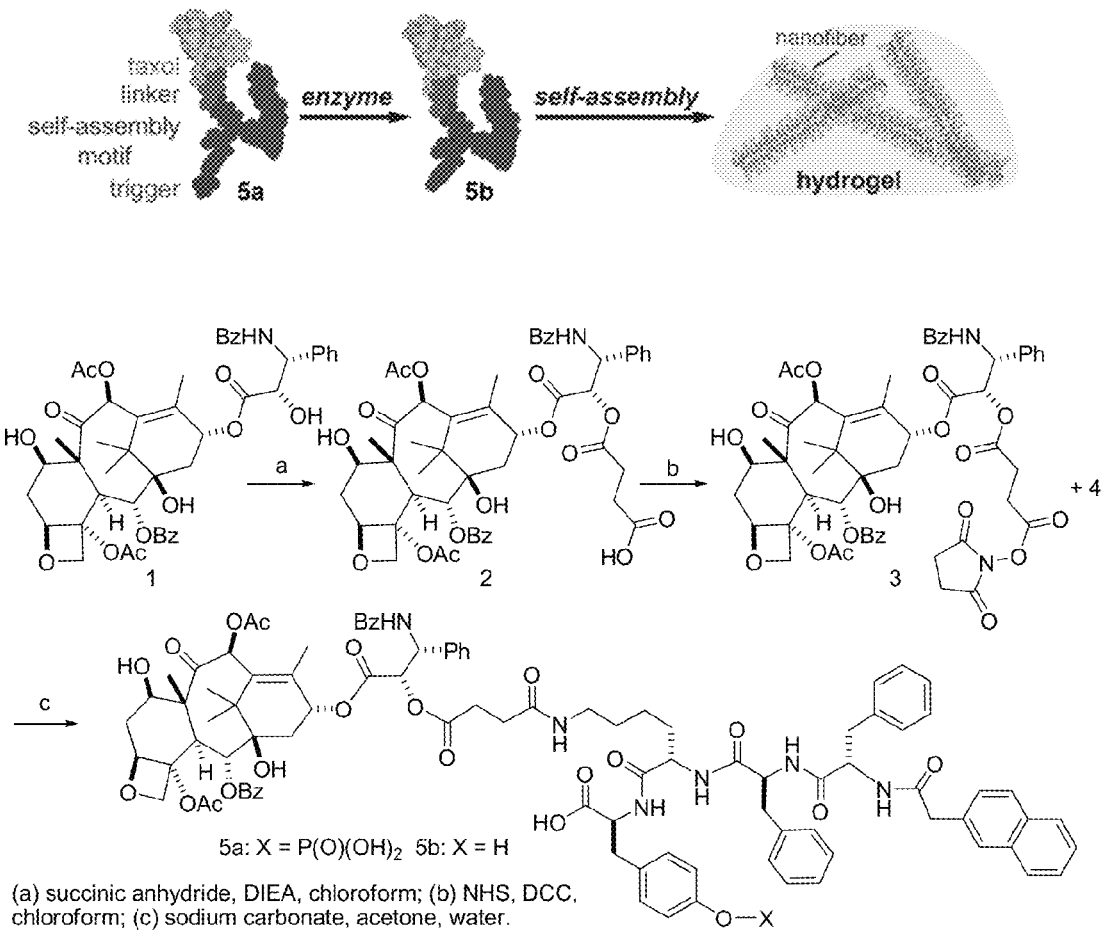
FIG. 1 depicts a graphical representation of the molecular process proposed to underlie the formation of a hydrogel; and an exemplary synthesis of a paclitaxel-containing (taxol-containing) compound of the invention.
Figure 1:
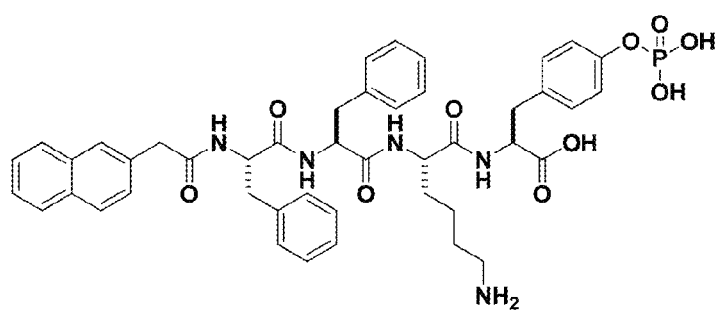

To connect paclitaxel covalently with a motif that tends to self-assemble and a group that is cleavable by an enzyme, a precursor for producing a paclitaxel hydrogel was designed and synthesized. As illustrated in FIG. 1 (top), upon the action of an enzyme, the precursor (5a) transforms into a hydrogelator (5b), which self-assembles into nanofibers and affords a supramolecular hydrogel of paclitaxel. The hydrogel can slowly releases the hydrogelator (5b) into an aqueous medium. Besides representing the first example of enzyme-instructed self-assembly and hydrogelation of complex, bioactive small molecules, this result demonstrates a new, facile way to formulate highly hydrophobic drugs, such as paclitaxel, into an aqueous form (e.g., hydrogel) without comprising their activities, and promises a general methodology to create therapeutic molecules that have a dual role as the delivery vehicle and the drug itself.

FIG. 1 (bottom) shows the synthetic route and the structure of the precursor (5a), which consists of a self-assembly motif, an enzyme-cleavable group, a linker, and a paclitaxel molecule. Yang, Z. M.; Gu, H. W.; Fu, D. G.; Gao, P.; Lam, J. K.; Xu, B. *Adv. Mater.* 2004, 16, 1440; and Yang, Z. M.; Liang, G. L.; Wang, L.; Bing, X. *J. Am. Chem. Soc.* 2006, 128, 3038. Based on the study of the structure-activity of paclitaxel derivatives, a linker (succinic acid) was connected to the C2' hydroxyl group of paclitaxel (1) to provide an intermediate (2), which was activated by N-hydroxysuccinimide (NHS) to afford 3. Guerittevoegelein, F.; Guenard, D.; Lavelle, F.; Legoff, M. T.; Mangatal, L.; Potier, P. *J. Med. Chem.* 1991, 34, 992; Swindell, C. S.; Krauss, N. E.; Horwitz, S. B.; Ringel, I. *J. Med. Chem.* 1991, 34, 1176; and Dosio, F.; Brusa, P.; Crosasso, P.; Arpicco, S.; Cattel, L. *J. Control. Rel.* 1997, 47, 293. The reaction of 3 with a phosphatase substrate (NapFFKYp, 4) that consists of the self-assembly motif and the enzyme-cleavable group affords the precursor (5a) in an overall yield of 37.1%. Additional details are provided below.

Compared to paclitaxel and the pyridinium paclitaxel pro-drug, the precursor (5a) exhibits much better solubility (7.6 mg/mL or 4.26 mM in a 100 mM phosphate buffered saline (PBS) solution) and has the distribution coefficient (octanol/water) of 0.61. Nicolaou, K. C.; Guy, R. K.; Pitsinos, E. N.; Wrasidlo, W. *Angew. Chem. Intl. Ed.* 1994, 33, 1583; U.S. Pat. No. 6,271,384 to Nicolaou et al.; and PCT Application No. PCT/US95/00538 to Nicolaou et al. In addition, the precursor (5a) has excellent stability in water and shows hardly any dephosphorylation over months without a phosphatase.

After dissolving 10 mg of the precursor (5a) into 1 mL of water at a pH of about 7.3 with the aid of sonication (FIG. 2A), 5 μL of alkaline phosphatase (10 U/μL) was added into the solution. The solution becomes slightly turbid (FIG. 2B) 5 minutes after the addition of the enzyme and turns into a translucent hydrogel (Gel 5b, FIG. 2C) overnight. LC-MS and HPLC traces confirmed the complete conversion of 5a to 5b in the hydrogel. Moreover, mass spectroscopic (MS) analysis indicates that 5b is stable in gel state over weeks, an important prerequisite for the sustained release of 5b from its own hydrogel (vide infra).

Figure 2:
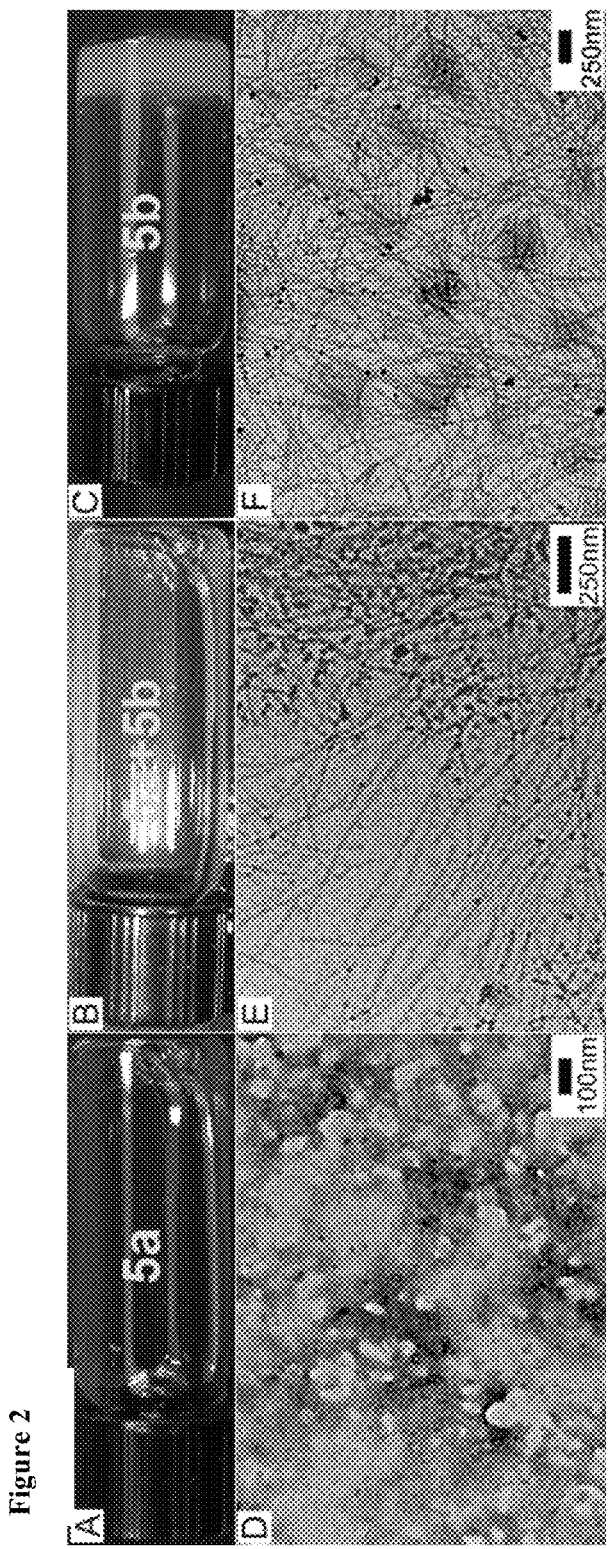
FIG. 2 depicts optical (A-C) and the corresponding transmission electron microscopic (TEM) images (D-F) of (A, D) the solution of 5a with [5a]=1.0 wt %; (B, E) the solution of 5a at 5 minutes after the addition of the alkaline phosphatase; and (C, F) the hydrogel of 5b overnight after the addition of the enzyme.

As shown in the TEM image (FIG. 2D), the solution of 5a gives featureless aggregates after cryo-drying. According to the TEM in FIG. 2E, five minutes after the addition of the enzyme, the mixture already contains the nanofibers with a width of 20 nm besides particle aggregates. Apparently, the nanofibers stretch out of the amorphous area, suggesting that the nanofibers grow from the enzymes. This is consistent with the enzyme-catalyzed self-assembly process. While the scanning electron micrograph (SEM) shows lamellar microstructures, the cryo-dried Gel 5b exhibits well-dispersed nanofiber networks with the uniform fiber width of 29 nm (FIG. 2F). These results confirm the self-assembly and formation of the nanofibers upon enzyme catalysis. Circular dichroism (CD) spectra of the solution of 5a and the corresponding Gel 5b further help elucidate the molecular arrangement of 5b in gel phase. The spectrum of Gel 5b exhibits a positive band near 192 nm ($\pi\pi^*$ transition of the amide bonds) and a broad negative band near 216 nm ($n\pi^*$ transition of the amide bonds and $\pi\pi^*$ of the naphthyl aromatics), coinciding with the CD of NapFFEGY 17 and indicating the existence of β-sheet like features. Moreover, the intensity of the peak at 298 nm, a characteristic peak of paclitaxel, decreases dramatically in the CD spectrum of Gel 5b in comparison with that of the solution of 5a, indicating that the 5b nanofibers might align in such a way to force the intrinsic dipole transition moments of the paclitaxels to opposite directions to reduce each other. This observation is consistent with traditional antiparallel arrangements in a β-sheet like secondary structures.

Figure 3:
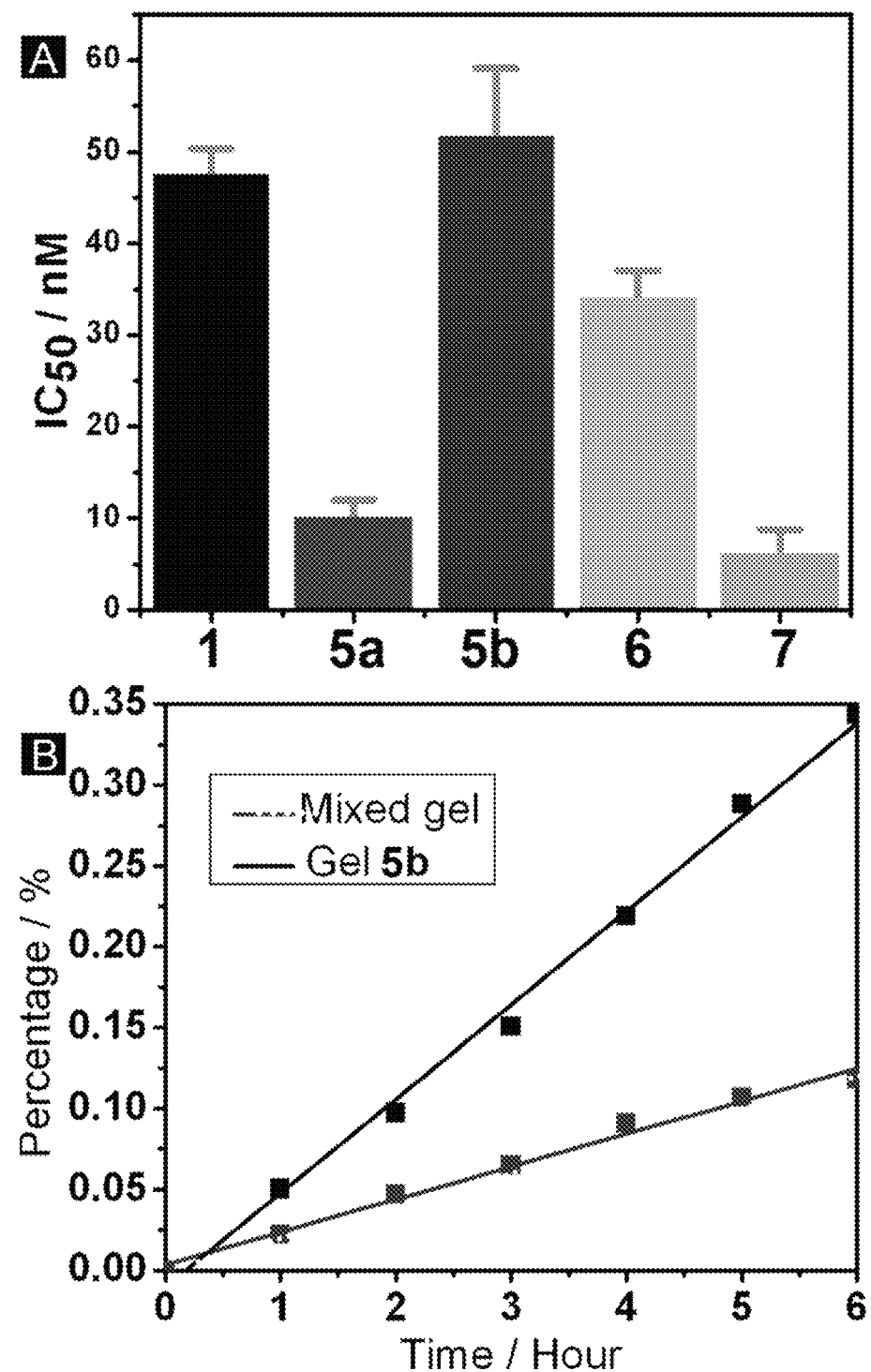
FIG. 3 depicts (A) the results of a cytotoxicity study of paclitaxel (1), 5a, 5b, paclitaxel-FFFFYp-OH (6) and a paclitaxel dimer (7) against HeLa cells and depicts (B) accumulative drug release profile of two kinds of paclitaxel gels in 100 nM PBS buffers.

To evaluate the activity of 5a, it was used to treat HeLa cells; paclitaxel (1) was used as the control. As shown in FIG. 3a, after 48 h of incubation with HeLa cells, 5a exhibits an $IC_{50}$ value of 9.97±2.05 nM, about five times lower than that of 1 (47.3±2.99 nM). Further examination shows the phosphatase substrate (4), is essentially biocompatible ($IC_{50}$ greater than about 500 µM). 5b itself exhibits $IC_{50}$ of 51.4±7.69 nM, which is comparable to that of 1. These results indicate that the activity of paclitaxel is conserved successfully in the precursor and the hydrogelator. One possible explanation for the higher activity of 5a than that of 5b in the cell assay might be the improved solubility of 5a.

The poor solubility of 5b (21.6 µg/mL or 12.66 µM) in water, unfortunately, prevents it from forming a hydrogel directly from 5b by changing temperature or pH. However, it is easy to generate hydrogels that consist of or contain 5b by enzymatic dephosphorylation of 5a, which allows one to evaluate the release of 5b from the hydrogels. FIG. 3B shows the release profiles of 5b from two kinds of gels: Gel 5b resulted from treating the solution of 5a (0.8 wt %) with alkaline phosphatase; and a mixed gel made by adding alkaline phosphatase into the solution of 5a (0.6 wt %) and 4 (0.6 wt %). When contacted with a fresh PBS buffer solution, Gel 5b and the mixed gel release 5b at the rates of 0.05% and 0.016% per hour, respectively. This experiment demonstrates the sustained release of 5b from its own gel and shows a way for the release rate control via the concentration of 5b in the mixed gel.

Selected Precursors and Gelators, and Nanofibers and Hydrogels Made Therefrom

One aspect of the invention relates to a compound represented by formula I:

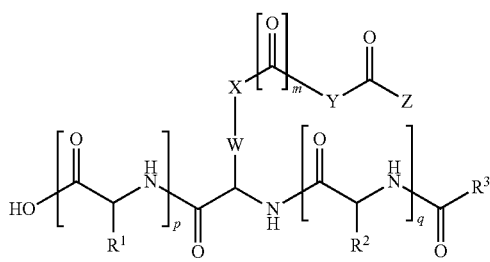

wherein, independently for each occurrence, $R^1$ is

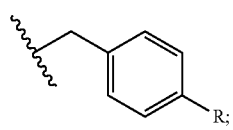

R is —H, —OH or —OPO$_3$H$_2$;

p is 0-8;

$R^2$ is

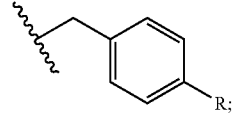

q is 0-8;

$R^3$ is aryl, aralkyl, heteroaryl, or heteroaralkyl;

W is ($C_1$-$C_{10}$)alkylene;

X is —O—, —N(H)—, —S— or —CH$_2$—;

m is 0 or 1;

Y is ($C_1$-$C_{10}$)alkylene; and

Z is bioactive small molecule;

provided that the sum of p and q is 2, 3, 4, 5, 6, 7 or 8; and at least one instance of R is —OH or —OPO$_3$H$_2$.

In certain embodiments, the present invention relates to any one of the aforementioned compounds, wherein p is 0. In certain embodiments, the present invention relates to any one of the aforementioned compounds, wherein p is 1. In certain embodiments, the present invention relates to any one of the aforementioned compounds, wherein p is 2. In certain embodiments, the present invention relates to any one of the aforementioned compounds, wherein p is 3. In certain embodiments, the present invention relates to any one of the aforementioned compounds, wherein p is 4. In certain embodiments, the present invention relates to any one of the aforementioned compounds, wherein p is 5. In certain embodiments, the present invention relates to any one of the aforementioned compounds, wherein p is 6. In certain embodiments, the present invention relates to any one of the aforementioned compounds, wherein p is 7. In certain embodiments, the present invention relates to any one of the aforementioned compounds, wherein p is 8.

In certain embodiments, the present invention relates to any one of the aforementioned compounds, wherein q is 0. In certain embodiments, the present invention relates to any one of the aforementioned compounds, wherein q is 1. In certain embodiments, the present invention relates to any one of the aforementioned compounds, wherein q is 2. In certain embodiments, the present invention relates to any one of the aforementioned compounds, wherein q is 3. In certain embodiments, the present invention relates to any one of the aforementioned compounds, wherein q is 4. In certain embodiments, the present invention relates to any one of the aforementioned compounds, wherein q is 5. In certain embodiments, the present invention relates to any one of the aforementioned compounds, wherein q is 6. In certain embodiments, the present invention relates to any one of the aforementioned compounds, wherein q is 7. In certain embodiments, the present invention relates to any one of the aforementioned compounds, wherein q is 8.

In certain embodiments, the present invention relates to any one of the aforementioned compounds, wherein only one instance of R is —OPO$_3$H$_2$.

In certain embodiments, the present invention relates to any one of the aforementioned compounds, wherein only one instance of R is —OPO$_3$H$_2$; and all other instances of R are —H.

In certain embodiments, the present invention relates to any one of the aforementioned compounds, wherein only one instance of R is —OH.

In certain embodiments, the present invention relates to any one of the aforementioned compounds, wherein only one instance of R is —OH; and all other instances of R are —H.

In certain embodiments, the present invention relates to any one of the aforementioned compounds, wherein one $R^1$ is

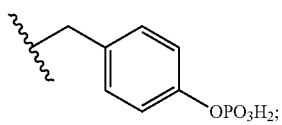

and the remaining instances of $R^1$, if any, and $R^2$, if any, are

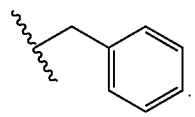 [SMILES: *Cc1ccccc1]

In certain embodiments, the present invention relates to any one of the aforementioned compounds, wherein one $R^2$ is

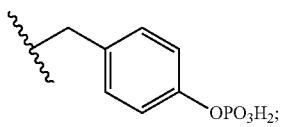

and the remaining instances of $R^2$, if any, and $R^1$, if any, are

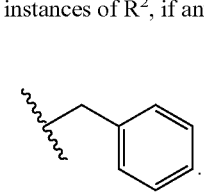

In certain embodiments, the present invention relates to any one of the aforementioned compounds, wherein one $R^1$ is

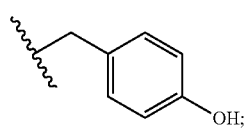

and the remaining instances of $R^1$, if any, and $R^2$, if any, are

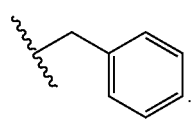

In certain embodiments, the present invention relates to any one of the aforementioned compounds, wherein one $R^2$ is

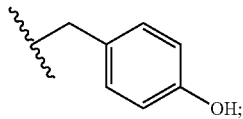

and the remaining instances of $R^2$, if any, and $R^1$, if any, are

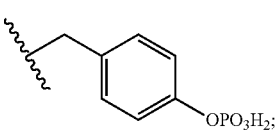

In certain embodiments, the present invention relates to any one of the aforementioned compounds, wherein $R^1$ is

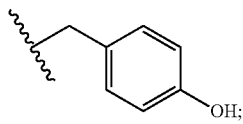

and p is 1.

In certain embodiments, the present invention relates to any one of the aforementioned compounds, wherein $R^1$ is

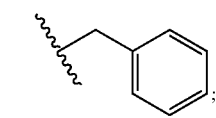

and p is 1.

In certain embodiments, the present invention relates to any one of the aforementioned compounds, wherein $R^2$ is

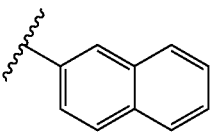

and q is 2.

In certain embodiments, the present invention relates to any one of the aforementioned compounds, wherein $R^3$ is

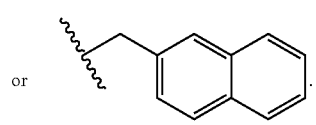

In certain embodiments, the present invention relates to any one of the aforementioned compounds, wherein R³ is

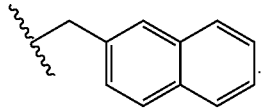 [SMILES: *Cc1ccc2ccccc2c1]

In certain embodiments, the present invention relates to any one of the aforementioned compounds, wherein W is —CH₂—, —CH₂CH₂—, —CH₂CH₂CH₂—, —CH₂CH₂CH₂CH₂—, —CH₂CH₂CH₂CH₂CH₂— or —CH₂CH₂CH₂CH₂CH₂CH₂—.

In certain embodiments, the present invention relates to any one of the aforementioned compounds, wherein W is —CH₂CH₂CH₂CH₂—.

In certain embodiments, the present invention relates to any one of the aforementioned compounds, wherein X is O.

In certain embodiments, the present invention relates to any one of the aforementioned compounds, wherein Y is —CH₂—, —CH₂CH₂—, —CH₂CH₂CH₂—, —CH₂CH₂CH₂CH₂—, —CH₂CH₂CH₂CH₂CH₂— or —CH₂CH₂CH₂CH₂CH₂CH₂—.

In certain embodiments, the present invention relates to any one of the aforementioned compounds, wherein Y is —CH₂CH₂—.

In certain embodiments, the present invention relates to any one of the aforementioned compounds, wherein m is 0.

In certain embodiments, the present invention relates to any one of the aforementioned compounds, wherein m is 1.

In certain embodiments, the present invention relates to any one of the aforementioned compounds, wherein Z is an antineoplastic agent.

In certain embodiments, the present invention relates to any one of the aforementioned compounds, wherein Z is paclitaxel, doxorubicin, daunorubicin, vinblastine, vincristine, cisplatin or 5-fluorouracil.

In certain embodiments, the present invention relates to any one of the aforementioned compounds, wherein —C(=O)—Z is

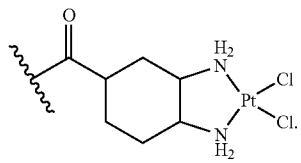

In certain embodiments, the present invention relates to any one of the aforementioned compounds, wherein —C(=O)—Z is

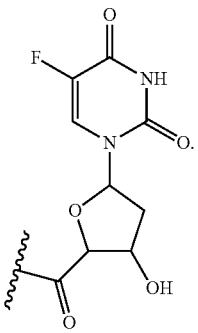 [SMILES: *C(=O)C1OC(n2cc(F)c(=O)[nH]c2=O)CC1O]

In certain embodiments, the present invention relates to any one of the aforementioned compounds, wherein —C(=O)—Z is

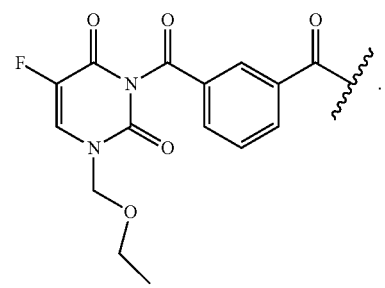

In certain embodiments, the present invention relates to any one of the aforementioned compounds, wherein Z

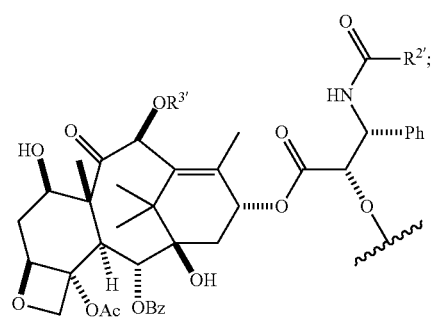

R²' is -Ph or —OtBu; and R³' is —H or —C(=O)CH₃.

In certain embodiments, the present invention relates to any one of the aforementioned compounds, wherein Z is

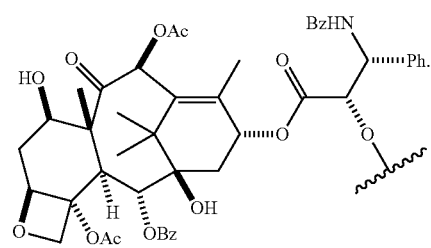

In certain embodiments, the present invention relates to any one of the aforementioned compounds, wherein Z is

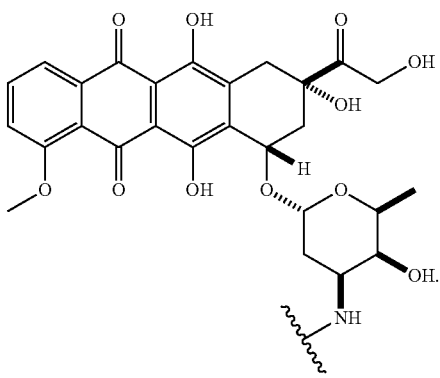

In certain embodiments, the present invention relates to any one of the aforementioned compounds, wherein Z is

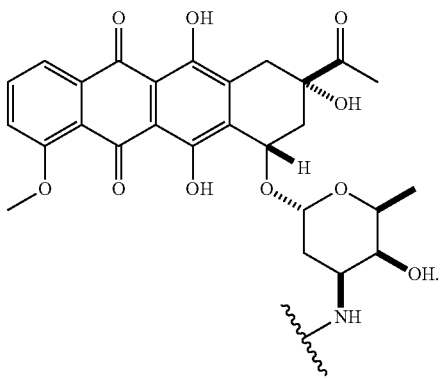

Another aspect of the invention relates to a compound of formula II:

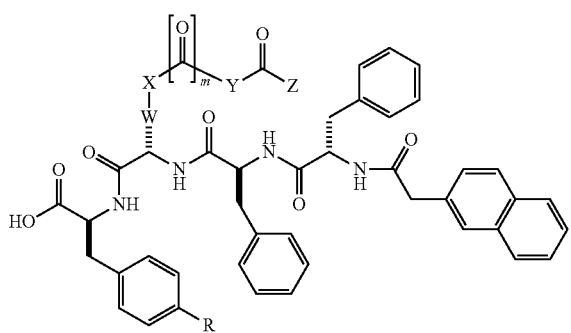

wherein, independently for each occurrence,
R is —OH or —OPO$_3$H$_2$;
W is (C$_1$-C$_{10}$)alkylene;
X is —O—, —N(H)—, —S— or —CH$_2$—;
m is 0 or 1;
Y is (C$_1$-C$_{10}$)alkylene; and
Z is bioactive small molecule.

In certain embodiments, the present invention relates to any one of the aforementioned compounds, wherein R is —OH.

In certain embodiments, the present invention relates to any one of the aforementioned compounds, wherein R is —OPO$_3$H$_2$.

In certain embodiments, the present invention relates to any one of the aforementioned compounds, wherein W is —CH$_2$—, —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$— or —CH$_2$CH$_2$CH$_2$CH$_2$CH$_2$CH$_2$—.

In certain embodiments, the present invention relates to any one of the aforementioned compounds, wherein W is —CH$_2$CH$_2$CH$_2$CH$_2$—.

In certain embodiments, the present invention relates to any one of the aforementioned compounds, wherein X is O.

In certain embodiments, the present invention relates to any one of the aforementioned compounds, wherein Y is —CH$_2$—, —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$— or —CH$_2$CH$_2$CH$_2$CH$_2$CH$_2$CH$_2$—.

In certain embodiments, the present invention relates to any one of the aforementioned compounds, wherein Y is —CH$_2$CH$_2$—.

In certain embodiments, the present invention relates to any one of the aforementioned compounds, wherein m is 0.

In certain embodiments, the present invention relates to any one of the aforementioned compounds, wherein m is 1.

In certain embodiments, the present invention relates to any one of the aforementioned compounds, wherein Z is an antineoplastic agent.

In certain embodiments, the present invention relates to any one of the aforementioned compounds, wherein Z is paclitaxel, doxorubicin, daunorubicin, vinblastine, vincristine, cisplatin or 5-fluorouracil.

In certain embodiments, the present invention relates to any one of the aforementioned compounds, wherein —C(=O)—Z is

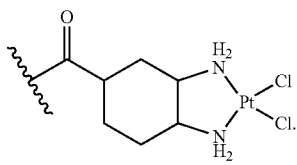

In certain embodiments, the present invention relates to any one of the aforementioned compounds, wherein —C(=O)—Z is

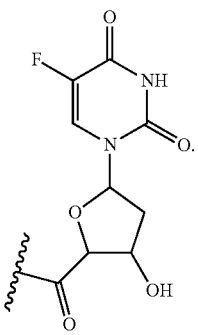 [SMILES: *C(=O)C1OC(n2cc(F)c(=O)[nH]c2=O)CC1O]

In certain embodiments, the present invention relates to any one of the aforementioned compounds, wherein —C(=O)—Z is

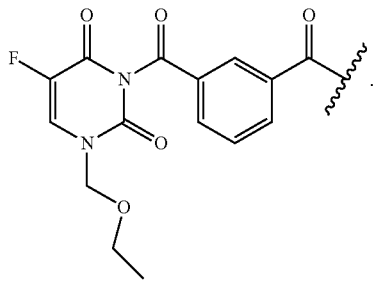 [SMILES: *C(=O)c1cccc(C(=O)n2c(=O)c(F)cn(COCC)c2=O)c1]

In certain embodiments, the present invention relates to any one of the aforementioned compounds, wherein Z is

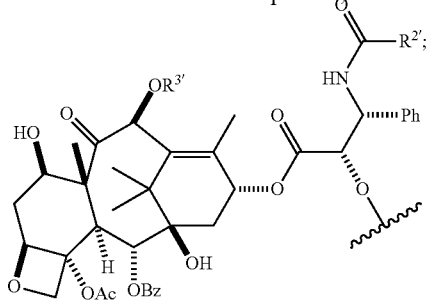

$R^{2'}$ is -Ph or —OtBu; and $R^{3'}$ is —H or —C(=O)CH$_3$.

In certain embodiments, the present invention relates to any one of the aforementioned compounds, wherein Z is

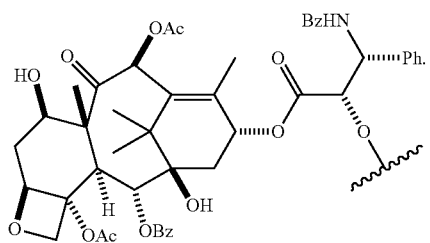

In certain embodiments, the present invention relates to any one of the aforementioned compounds, wherein Z is

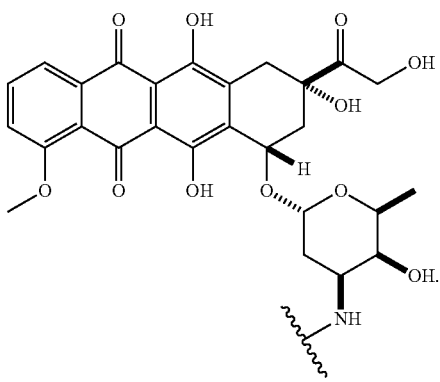

In certain embodiments, the present invention relates to any one of the aforementioned compounds, wherein Z is

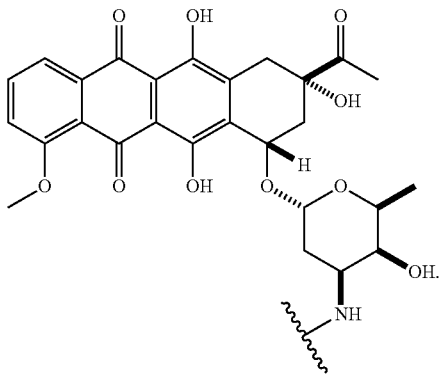

In certain embodiments, the present invention relates to any one of the aforementioned compounds, wherein R is —OH; X is O; and m is 1.

In certain embodiments, the present invention relates to any one of the aforementioned compounds, wherein R is —OPO$_3$H$_2$; X is O; and m is 1.

In certain embodiments, the present invention relates to any one of the aforementioned compounds, wherein R is —OH; W is —CH$_2$CH$_2$CH$_2$CH$_2$—; X is O; Y is —CH$_2$CH$_2$—; and m is 1.

In certain embodiments, the present invention relates to any one of the aforementioned compounds, wherein R is —OPO$_3$H$_2$; W is —CH$_2$CH$_2$CH$_2$CH$_2$—; X is O; Y is —CH$_2$CH$_2$—; and m is 1.

In certain embodiments, the present invention relates to any one of the aforementioned compounds, wherein R is —OH; W is —CH$_2$CH$_2$CH$_2$CH$_2$—; X is O; Y is —CH$_2$CH$_2$—; m is 1; and Z is

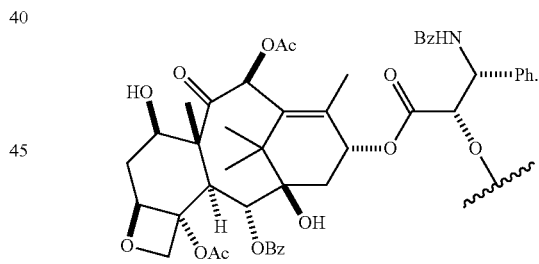

In certain embodiments, the present invention relates to any one of the aforementioned compounds, wherein R is —OPO$_3$H$_2$; W is —CH$_2$CH$_2$CH$_2$CH$_2$—; X is O; Y is —CH$_2$CH$_2$—; m is 1; and Z is

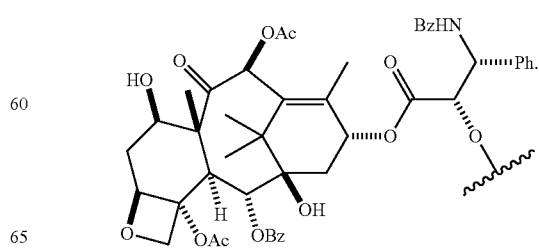

Certain compounds of the invention which have acidic substituents may exist as salts with pharmaceutically acceptable bases. The present invention includes such salts. Examples of such salts include sodium salts, potassium salts, lysine salts and arginine salts. These salts may be prepared by methods known to those skilled in the art.

Certain compounds of the invention and their salts may exist in more than one crystal form and the present invention includes each crystal form and mixtures thereof.

Certain compounds of the invention and their salts may also exist in the form of solvates, for example hydrates, and the present invention includes each solvate and mixtures thereof.

Certain compounds of the invention may contain one or more chiral centers, and exist in different optically active forms. When compounds of the invention contain one chiral center, the compounds exist in two enantiomeric forms and the present invention includes both enantiomers and mixtures of enantiomers, such as racemic mixtures. The enantiomers may be resolved by methods known to those skilled in the art, for example by formation of diastereoisomeric salts which may be separated, for example, by crystallization; formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step may be used to liberate the desired enantiomeric form. Alternatively, specific enantiomers may be synthesized by asymmetric synthesis using optically active reagents, substrates, catalysts or solvents, or by converting one enantiomer into the other by asymmetric transformation.

When a compound of the invention contains more than one chiral center, it may exist in diastereoisomeric forms. The diastereoisomeric compounds may be separated by methods known to those skilled in the art, for example chromatography or crystallization and the individual enantiomers may be separated as described above. The present invention includes each diastereoisomer of compounds of the invention and mixtures thereof.

Certain compounds of the invention may exist in different tautomeric forms or as different geometric isomers, and the present invention includes each tautomer and/or geometric isomer of compounds of the invention and mixtures thereof.

Certain compounds of the invention may exist in different stable conformational forms which may be separable. Torsional asymmetry due to restricted rotation about an asymmetric single bond, for example because of steric hindrance or ring strain, may permit separation of different conformers. The present invention includes each conformational isomer of compounds of the invention and mixtures thereof.

Certain compounds of the invention may exist in zwitterionic form and the present invention includes each zwitterionic form of compounds of the invention and mixtures thereof.

Another aspect of the invention relates to a self-assembled molecular nanofiber, comprising a plurality of any one of the aforementioned compounds, wherein at least one instance of R is —OH.

Another aspect of the invention relates to a self-assembled molecular nanofiber consisting essentially of a plurality any one of the aforementioned compounds wherein at least one instance of R is —OH.

Another aspect of the invention relates to a self-assembled molecular nanofiber, comprising a plurality of any one of the aforementioned compounds, wherein at least one instance of R is —OH; and a plurality of NapFFKY.

Another aspect of the invention relates to a self-assembled molecular nanofiber, consisting essentially of a plurality of any one of the aforementioned compounds, wherein at least one instance of R is —OH; and a plurality of NapFFKY.

Another aspect of the invention relates to a supramolecular hydrogel comprising any one of the aforementioned self-assembled molecular nanofibers.

Another aspect of the invention relates to a supramolecular hydrogel consisting essentially of any one of the aforementioned self-assembled molecular nanofibers.

In certain embodiments, the present invention relates to any one of the aforementioned compounds or supramolecular hydrogels for use in the treatment of cancer, tumors, malignancies, neoplasms, or other dysproliferative diseases.

In certain embodiments, the present invention relates to any one of the aforementioned compounds or supramolecular hydrogels for use in the manufacture of a medicament for treating cancer, tumors, malignancies, neoplasms, or other dysproliferative diseases.

Examples of cancers, tumors, malignancies, neoplasms, and other dysproliferative diseases that can be treated according to the invention include leukemias, such as myeloid and lymphocytic leukemias, lymphomas, myeloproliferative diseases, and solid tumors, such as but not limited to sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma.

Pharmaceutical Compositions

One or more compounds of this invention can be administered to a human patient alone or in pharmaceutical compositions where they are mixed with biologically suitable carriers or excipient(s) at doses to treat or ameliorate a disease or condition as described herein. Mixtures of these compounds can also be administered to the patient as a simple mixture or in suitable formulated pharmaceutical compositions. For example, one aspect of the invention relates to pharmaceutical composition comprising a therapeutically effective dose of a compound of formula I or II, a nanofiber or gel prepared therefrom, or a pharmaceutically acceptable salt, biologically active metabolite, solvate, hydrate, prodrug, enantiomer or stereoisomer thereof; and a pharmaceutically acceptable diluent or carrier.

As used herein, a therapeutically effective dose refers to that amount of the compound or compounds sufficient to result in the prevention or attenuation of a disease or condition as described herein. Techniques for formulation and administration of the compounds of the instant application may be found in references well known to one of ordinary skill in the art, such as "Remington's Pharmaceutical Sciences," Mack Publishing Co., Easton, Pa., latest edition.

Suitable routes of administration may, for example, include oral, eyedrop, rectal, transmucosal, topical, or intestinal administration; parenteral delivery, including intramuscular, subcutaneous, intramedullary injections, as well as intrathecal, direct intraventricular, intravenous, intraperitoneal, intranasal, or intraocular injections.

Alternatively, one may administer the compound in a local rather than a systemic manner, for example, via injection of the compound directly into an edematous site.

Furthermore, one may administer the drug in a targeted drug delivery system, for example, in a liposome coated with endothelial cell-specific antibody.

The pharmaceutical compositions of the present invention may be manufactured in a manner that is itself known, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in a conventional manner using one or more physiologically acceptable carriers comprising excipients and auxiliaries which facilitate processing of the active compounds into preparations which can be used pharmaceutically. Proper formulation is dependent upon the route of administration chosen.

For injection, the agents of the invention may be formulated in aqueous solutions, preferably in physiologically compatible buffers such as Hanks' solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained by combining the active compound with a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

The compounds can be formulated for parenteral administration by injection, e.g., bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly or by intramuscular injection). Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Alternatively, other delivery systems for hydrophobic pharmaceutical compounds may be employed. Liposomes and emulsions are well known examples of delivery vehicles or carriers for hydrophobic drugs. Certain organic solvents such as dimethysulfoxide also may be employed, although usually at the cost of greater toxicity. Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Many one of the compounds of the invention may be provided as salts with pharmaceutically compatible counterions (i.e., pharmaceutically acceptable salts). A "pharmaceutically acceptable salt" means any non-toxic salt that, upon administration to a recipient, is capable of providing, either directly or indirectly, a compound or a prodrug of a compound of this invention. A "pharmaceutically acceptable counterion" is an ionic portion of a salt that is not toxic when released from the salt upon administration to a recipient. Pharmaceutically compatible salts may be formed with many acids, including but not limited to hydrochloric, sulfuric, acetic, lactic, tartaric, malic, succinic, etc. Salts tend to be more soluble in aqueous or other protonic solvents than are the corresponding free base forms.

Acids commonly employed to form pharmaceutically acceptable salts include inorganic acids such as hydrogen bisulfide, hydrochloric, hydrobromic, hydroiodic, sulfuric and phosphoric acid, as well as organic acids such as para-toluenesulfonic, salicylic, tartaric, bitartaric, ascorbic, maleic, besylic, fumaric, gluconic, glucuronic, formic, glutamic, methanesulfonic, ethanesulfonic, benzenesulfonic, lactic, oxalic, para-bromophenylsulfonic, carbonic, succinic, citric, benzoic and acetic acid, and related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephathalate, sulfonate, xylenesulfonate, phenylacetate, phenylpropionate, phenylbutyrate, citrate, lactate, .beta.-hydroxybutyrate, glycolate, maleate, tartrate, methanesulfonate, propanesulfonate, naphthalene-1-sulfonate, naphthalene-2-sulfonate, mandelate and the like salts. Preferred pharmaceutically acceptable acid addition salts include those formed with mineral acids such as hydrochloric acid and hydrobromic acid, and especially those formed with organic acids such as maleic acid.

Suitable bases for forming pharmaceutically acceptable salts with acidic functional groups include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl,N-ethylamine; diethylamine; triethylamine; mono-, bis-, or tris-(2-hydroxy-lower alkyl amines), such as mono-, bis-, or tris-(2-hydroxyethyl)amine, 2-hydroxy-tert-butylamine, or tris-(hydroxymethyl)methylamine, N,N-di alkyl-N-(hydroxy alkyl)-amines, such as N,N-dimethyl-N-(2-hydroxyethyl)amine, or tri-(2-hydroxyethyl)amine; N-methyl-D-glucamine; and amino acids such as arginine, lysine, and the like.

Pharmaceutical compositions suitable for use in the present invention include compositions wherein the active ingredients are contained in an effective amount to achieve its intended purpose. More specifically, a therapeutically effective amount means an amount effective to prevent development of or to alleviate the existing symptoms of the subject being treated. Determination of the effective amounts is well within the capability of those skilled in the art.

Selected Methods

One aspect of the invention relates to a method of treating cancer, tumors, malignancies, neoplasms, or other dysproliferative diseases, comprising administering to a patient in need thereof a therapeutically effective amount of a compound represented by formula I:

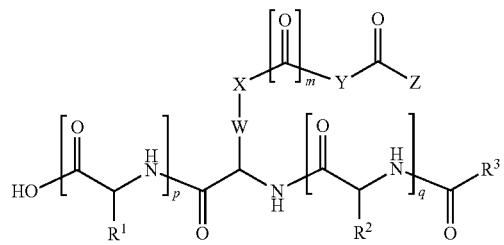

I wherein, independently for each occurrence,
$R^1$ is

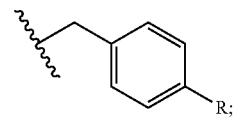

R is —H or —OPO$_3$H$_2$;
p is 0-8;
$R^2$ is

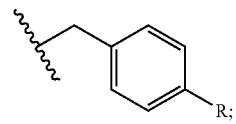

q is 0-8;
$R^3$ is aryl, aralkyl, heteroaryl, or heteroaralkyl;
W is $(C_1-C_{10})$alkylene;
X is —O—, —N(H)—, —S— or —CH$_2$—;
m is 0 or 1;
Y is $(C_1-C_{10})$alkylene; and
Z is bioactive small molecule;
provided that the sum of p and q is 2, 3, 4, 5, 6, 7 or 8; and at least one instance of R is —OPO$_3$H$_2$.

In certain embodiments, the present invention relates to any one of the aforementioned methods, wherein p is 0. In certain embodiments, the present invention relates to any one of the aforementioned methods, wherein p is 1. In certain embodiments, the present invention relates to any one of the aforementioned methods, wherein p is 2. In certain embodiments, the present invention relates to any one of the aforementioned methods, wherein p is 3. In certain embodiments, the present invention relates to any one of the aforementioned methods, wherein p is 4. In certain embodiments, the present invention relates to any one of the aforementioned methods, wherein p is 5. In certain embodiments, the present invention relates to any one of the aforementioned methods, wherein p is 6. In certain embodiments, the present invention relates to any one of the aforementioned methods, wherein p is 7. In certain embodiments, the present invention relates to any one of the aforementioned methods, wherein p is 8.

In certain embodiments, the present invention relates to any one of the aforementioned methods, wherein q is 0. In certain embodiments, the present invention relates to any one of the aforementioned methods, wherein q is 1. In certain embodiments, the present invention relates to any one of the aforementioned methods, wherein q is 2. In certain embodiments, the present invention relates to any one of the aforementioned methods, wherein q is 3. In certain embodiments, the present invention relates to any one of the aforementioned methods, wherein q is 4. In certain embodiments, the present invention relates to any one of the aforementioned methods, wherein q is 5. In certain embodiments, the present invention relates to any one of the aforementioned methods, wherein q is 6. In certain embodiments, the present invention relates to any one of the aforementioned methods, wherein q is 7. In certain embodiments, the present invention relates to any one of the aforementioned methods, wherein q is 8.

In certain embodiments, the present invention relates to any one of the aforementioned methods, wherein only one instance of R is —$OPO_3H_2$.

In certain embodiments, the present invention relates to any one of the aforementioned methods, wherein only one instance of R is —$OPO_3H_2$; and all other instances of R are —H.

In certain embodiments, the present invention relates to any one of the aforementioned methods, wherein one $R^1$ is

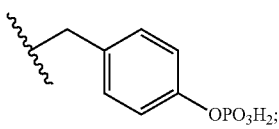

and the remaining instances of $R^1$, if any, and $R^2$, if any, are

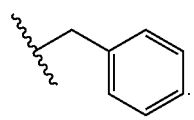 [SMILES: *Cc1ccccc1]

In certain embodiments, the present invention relates to any one of the aforementioned methods, wherein one $R^2$ is

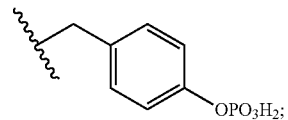

and the remaining instances of $R^2$, if any, and $R^1$, if any, are

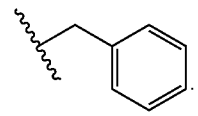

In certain embodiments, the present invention relates to any one of the aforementioned methods, wherein $R^1$ is

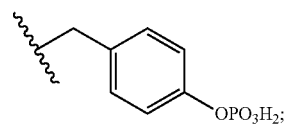

and p is 1.

In certain embodiments, the present invention relates to any one of the aforementioned methods, wherein $R^2$ is

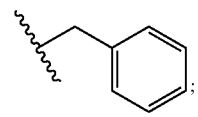 [SMILES: *Cc1ccccc1]

and q is 2.

In certain embodiments, the present invention relates to any one of the aforementioned methods, wherein $R^3$ is

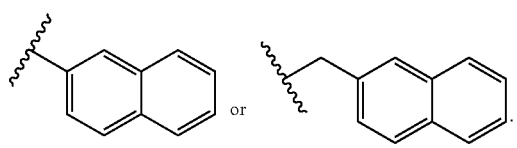 [SMILES: *c1ccc2ccccc2c1 ; *Cc1ccc2ccccc2c1]

In certain embodiments, the present invention relates to any one of the aforementioned methods, wherein $R^3$ is

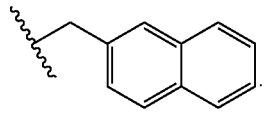 [SMILES: *Cc1ccc2ccccc2c1]

In certain embodiments, the present invention relates to any one of the aforementioned methods, wherein W is —$CH_2$—, —$CH_2CH_2$—, —$CH_2CH_2CH_2$—, —$CH_2CH_2CH_2CH_2$—, —$CH_2CH_2CH_2CH_2CH_2$— or —$CH_2CH_2CH_2CH_2CH_2CH_2$—.

In certain embodiments, the present invention relates to any one of the aforementioned methods, wherein W is —$CH_2CH_2CH_2CH_2$—.

In certain embodiments, the present invention relates to any one of the aforementioned methods, wherein X is O.

In certain embodiments, the present invention relates to any one of the aforementioned methods, wherein Y is —CH₂—, —CH₂CH₂—, —CH₂CH₂CH₂—, —CH₂CH₂CH₂CH₂—, —CH₂CH₂CH₂CH₂CH₂— or —CH₂CH₂CH₂CH₂CH₂CH₂—.

In certain embodiments, the present invention relates to any one of the aforementioned methods, wherein Y is —CH₂CH₂—.

In certain embodiments, the present invention relates to any one of the aforementioned methods, wherein m is 0.

In certain embodiments, the present invention relates to any one of the aforementioned methods, wherein m is 1.

In certain embodiments, the present invention relates to any one of the aforementioned methods, wherein Z is an antineoplastic agent.

In certain embodiments, the present invention relates to any one of the aforementioned methods, wherein Z is paclitaxel, doxorubicin, daunorubicin, vinblastine, vincristine, cisplatin or 5-fluorouracil.

In certain embodiments, the present invention relates to any one of the aforementioned methods, wherein —C(=O)—Z is

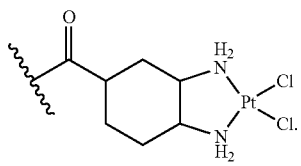

In certain embodiments, the present invention relates to any one of the aforementioned methods, wherein —C(=O)—Z is

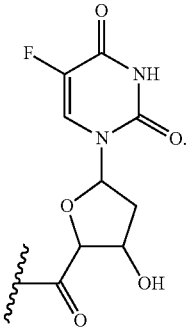 [SMILES: *C(=O)C1OC(n2cc(F)c(=O)[nH]c2=O)CC1O]

In certain embodiments, the present invention relates to any one of the aforementioned methods, wherein —C(=O)—Z is

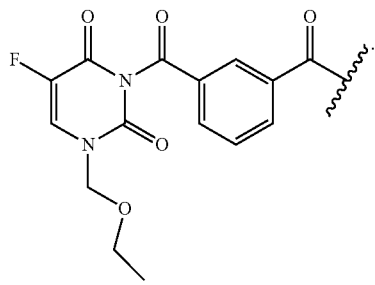 [SMILES: *C(=O)c1cccc(C(=O)n2c(=O)c(F)cn(COCC)c2=O)c1]

In certain embodiments, the present invention relates to any one of the aforementioned methods, wherein Z is

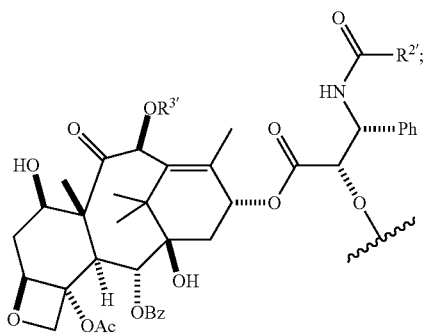

$R^{2'}$ is -Ph or —OtBu; and $R^{3'}$ is —H or —C(=O)CH₃.

In certain embodiments, the present invention relates to any one of the aforementioned methods, wherein Z is

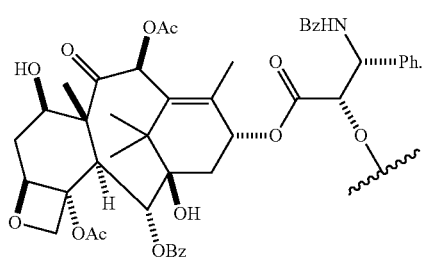

In certain embodiments, the present invention relates to any one of the aforementioned methods, wherein Z is

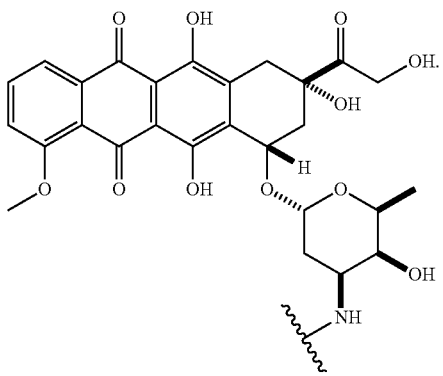

In certain embodiments, the present invention relates to any one of the aforementioned methods, wherein Z is

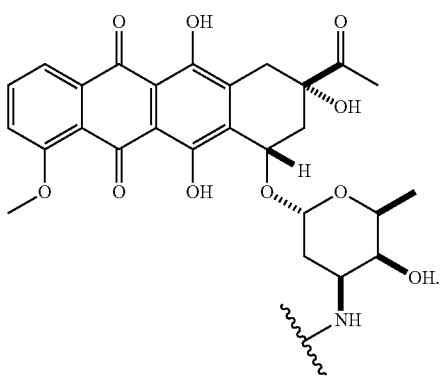

Another aspect of the invention relates to a method of treating cancer, tumors, malignancies, neoplasms, or other dysproliferative diseases, comprising administering to a patient in need thereof a therapeutically effective amount of a compound represented by formula II:

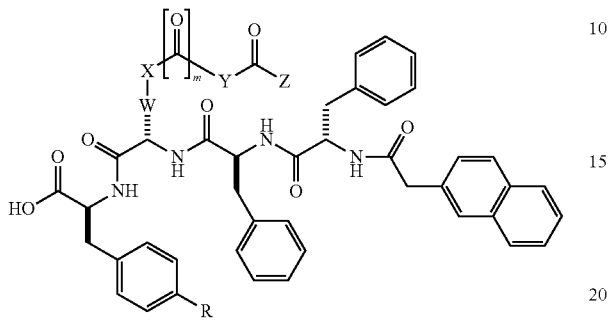

II wherein, independently for each occurrence,

R is —OPO$_3$H$_2$;

W is (C$_1$-C$_{10}$)alkylene;

X is —O—, —N(H)—, —S— or —CH$_2$—;

m is 0 or 1;

Y is (C$_1$-C$_{10}$)alkylene; and

Z is bioactive small molecule.

In certain embodiments, the present invention relates to any one of the aforementioned methods, wherein W is —CH$_2$—, —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$— or —CH$_2$CH$_2$CH$_2$CH$_2$CH$_2$CH$_2$—.

In certain embodiments, the present invention relates to any one of the aforementioned methods, wherein W is —CH$_2$CH$_2$CH$_2$CH$_2$—.

In certain embodiments, the present invention relates to any one of the aforementioned methods, wherein X is O.

In certain embodiments, the present invention relates to any one of the aforementioned methods, wherein Y is —CH$_2$—, —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$— or —CH$_2$CH$_2$CH$_2$CH$_2$CH$_2$CH$_2$—.

In certain embodiments, the present invention relates to any one of the aforementioned methods, wherein Y is —CH$_2$CH$_2$—.

In certain embodiments, the present invention relates to any one of the aforementioned methods, wherein m is 0.

In certain embodiments, the present invention relates to any one of the aforementioned methods, wherein m is 1.

In certain embodiments, the present invention relates to any one of the aforementioned methods, wherein Z is an antineoplastic agent.

In certain embodiments, the present invention relates to any one of the aforementioned methods, wherein Z is paclitaxel, doxorubicin, daunorubicin, vinblastine, vincristine, cisplatin or 5-fluorouracil.

In certain embodiments, the present invention relates to any one of the aforementioned methods, wherein —C(=O)—Z is

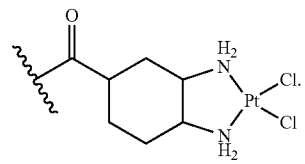

In certain embodiments, the present invention relates to any one of the aforementioned methods, wherein —C(=O)—Z is

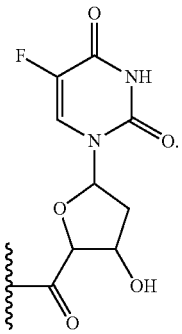 [SMILES: *C(=O)C1OC(n2cc(F)c(=O)[nH]c2=O)CC1O]

In certain embodiments, the present invention relates to any one of the aforementioned methods, wherein —C(=O)—Z is

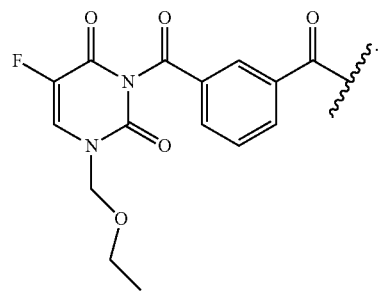 [SMILES: *C(=O)c1cccc(C(=O)n2c(=O)c(F)cn(COCC)c2=O)c1]

In certain embodiments, the present invention relates to any one of the aforementioned methods, wherein Z is

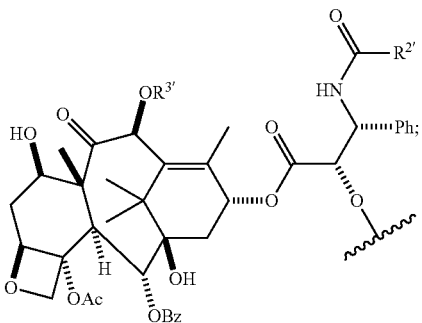

R$^{2'}$ is -Ph or —OtBu; and R$^{3'}$ is —H or —C(=O)CH$_3$.

In certain embodiments, the present invention relates to any one of the aforementioned methods, wherein Z is

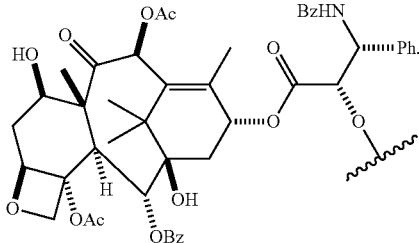

In certain embodiments, the present invention relates to any one of the aforementioned methods, wherein Z is

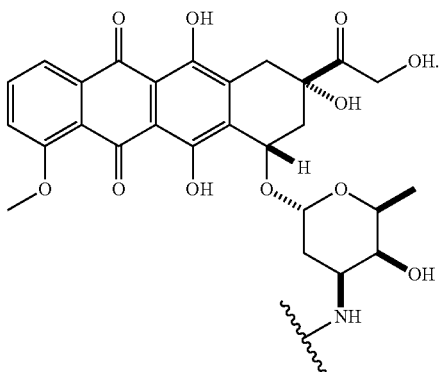

In certain embodiments, the present invention relates to any one of the aforementioned methods, wherein Z is

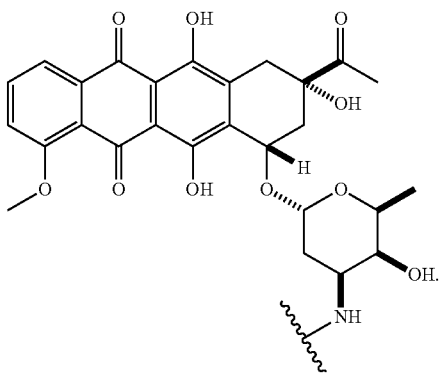

In certain embodiments, the present invention relates to any one of the aforementioned methods, wherein R is —$OPO_3H_2$; X is O; and m is 1.

In certain embodiments, the present invention relates to any one of the aforementioned methods, wherein R is —$OPO_3H_2$; W is —$CH_2CH_2CH_2CH_2$—; X is O; Y is —$CH_2CH_2$—; and m is 1.

In certain embodiments, the present invention relates to any one of the aforementioned methods, wherein R is —$OPO_3H_2$; W is —$CH_2CH_2CH_2CH_2$—; X is O; Y is —$CH_2CH_2$—; m is 1; and Z is

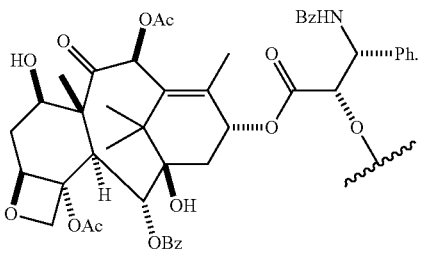

Examples of cancers, tumors, malignancies, neoplasms, and other dysproliferative diseases that can be treated according to the invention include leukemias, such as myeloid and lymphocytic leukemias, lymphomas, myeloproliferative diseases, and solid tumors, such as but not limited to sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma.

The systemic delivery of anticancer agents has been widely investigated but localized delivery may offer a safer and more effective delivery approach. The supramolecular hydrogels described above can be used to locally deliver antineoplastic agents.

One aspect of the invention relates to a method of treating cancer, tumors, malignancies, neoplasms, or other dysproliferative diseases by administering to a patient in need thereof any one of the aforementioned supramolecular hydrogels.

Selected Uses

In one embodiment, the present invention relates to the use of any one of the aforementioned compounds, supramolecular hydrogels, or pharmaceutical compositions, or pharmaceutically acceptable salts or solvates of any of them, in the manufacture of a medicament for the treatment of cancers, tumors, malignancies, neoplasms, or other dysproliferative diseases.

Examples of cancers, tumors, malignancies, neoplasms, and other dysproliferative diseases that can be treated according to the invention include leukemias, such as myeloid and lymphocytic leukemias, lymphomas, myeloproliferative diseases, and solid tumors, such as but not limited to sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma.

Combination Therapy

In one aspect of the invention, a compound of the invention, or a pharmaceutically acceptable salt thereof, can be used alone or in combination with another therapeutic agent to treat diseases such as cancer. It should be understood that the compounds of the invention can be used alone or in combination with an additional agent, e.g., a therapeutic agent, said additional agent being selected by the skilled artisan for its intended purpose. For example, the additional agent can be a therapeutic agent that is art-recognized as being useful to treat the disease or condition being treated by the compound of the present invention. The additional agent also can be an agent that imparts a beneficial attribute to the therapeutic composition e.g., an agent that affects the viscosity of the composition.

The combination therapy contemplated by the invention includes, for example, administration of a compound of the invention, or a pharmaceutically acceptable salt thereof, and additional agent(s) in a single pharmaceutical formulation as well as administration of a compound of the invention, or a pharmaceutically acceptable salt thereof, and additional agent(s) in separate pharmaceutical formulations. In other words, co-administration shall mean the administration of at least two agents to a subject so as to provide the beneficial effects of the combination of both agents. For example, the agents may be administered simultaneously or sequentially over a period of time.

It should further be understood that the combinations included within the invention are those combinations useful for their intended purpose. The combination can also include more than one additional agent, e.g., two or three additional agents if the combination is such that the formed composition can perform its intended function.

Dosage

As used herein, a "therapeutically effective amount" or "therapeutically effective dose" is an amount of a compound of the invention or a combination of two or more such compounds, which inhibits, totally or partially, the progression of the condition or alleviates, at least partially, one or more symptoms of the condition. A therapeutically effective amount can also be an amount which is prophylactically effective. The amount which is therapeutically effective will depend upon the patient's size and gender, the condition to be treated, the severity of the condition and the result sought. For a given patient, a therapeutically effective amount can be determined by methods known to those of skill in the art.

For any compound used in a method of the present invention, the therapeutically effective dose can be estimated initially from cellular assays. For example, a dose can be formulated in cellular and animal models to achieve a circulating concentration range that includes the $IC_{50}$ as determined in cellular assays (i.e., the concentration of the test compound which achieves a half-maximal inhibition). In some cases it is appropriate to determine the $IC_{50}$ in the presence of 3 to 5% serum albumin since such a determination approximates the binding effects of plasma protein on the compound. Such information can be used to more accurately determine useful doses in humans.

A therapeutically effective dose refers to that amount of the compound that results in amelioration of symptoms in a patient. Toxicity and therapeutic efficacy of such compounds can be determined by standard pharmaceutical procedures in cell cultures or experimental animals, e.g., for determining the maximum tolerated dose (MTD) and the $ED_{50}$ (effective dose for 50% maximal response). The dose ratio between toxic and therapeutic effects is the therapeutic index and it can be expressed as the ratio between MTD and $ED_{50}$. The data obtained from these cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition. (See e.g., Fingl et al., 1975, in "The Pharmacological Basis of Therapeutics", Ch. 1 p 1). In the treatment of crises, the administration of an acute bolus or an infusion approaching the MTD may be required to obtain a rapid response.

Dosage amount and interval may be adjusted individually to provide plasma levels of the active moiety which are sufficient to maintain the kinase modulating effects, or minimal effective concentration (MEC). The MEC will vary for each compound but can be estimated from in vitro data. Dosages necessary to achieve the MEC will depend on individual characteristics and route of administration. However, HPLC assays or bioassays can be used to determine plasma concentrations.

Dosage intervals can also be determined using the MEC value. Compounds should be administered using a regimen which maintains plasma levels above the MEC for 10-90% of the time, preferably between 30-90% and most preferably between 50-90% until the desired amelioration of symptoms is achieved. In cases of local administration or selective uptake, the effective local concentration of the drug may not be related to plasma concentration.

The amount of composition administered will, of course, be dependent on the subject being treated, on the subject's weight, the severity of the affliction, the manner of administration and the judgment of the prescribing physician.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. Compositions comprising a compound of the invention formulated in a compatible pharmaceutical carrier may also be prepared, placed in an appropriate container, and labeled for treatment of an indicated condition.

Definitions

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures.

For purposes of this invention, the chemical elements are identified in accordance with the Periodic Table of the Elements, CAS version, Handbook of Chemistry and Physics, 67th Ed., 1986-87, inside cover.

The term "amino acid" is intended to embrace all compounds, whether natural or synthetic, which include both an amino functionality and an acid functionality, including amino acid analogues and derivatives. In certain embodiments, the amino acids contemplated in the present invention are those naturally occurring amino acids found in proteins, or the naturally occurring anabolic or catabolic products of such amino acids, which contain amino and carboxyl groups.

Naturally occurring amino acids are identified throughout by the conventional three-letter and/or one-letter abbreviations, corresponding to the trivial name of the amino acid, in accordance with the following list: Alanine (Ala), Arginine (Arg), Asparagine (Asn), Aspartic acid (Asp), Cysteine (Cys), Glutamic acid (Glu), Glutamine (Gln), Glycine (Gly), Histidine (His), Isoleucine (Ile), Leucine (Leu), Lysine (Lys), Methionine (Met), Phenylalanine (Phe), Proline (Pro), Serine (Ser), Threonine (Thr), Tryptophan (Trp), Tyrosine (Tyr), and Valine (Val). The abbreviations are accepted in the peptide art and are recommended by the IUPAC-IUB commission in biochemical nomenclature. For example, the abbreviation "NapFFKYp" refers to the following compound:

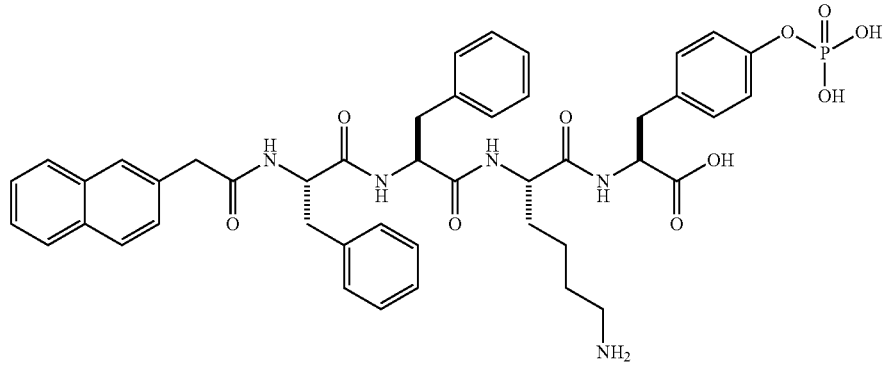 [SMILES: NCCCC[C@H](NC(=O)[C@H](Cc1ccccc1)NC(=O)[C@H](Cc1ccccc1)NC(=O)Cc1ccc2ccccc2c1)C(=O)N[C@@H](Cc1ccc(OP(=O)(O)O)cc1)C(=O)O]

and "NapFFKY" is the abbreviation for the corresponding dephosphorylated compound.

The term "amino acid" further includes analogues, derivatives, and congeners of any specific amino acid referred to herein, as well as C-terminal or N-terminal protected amino acid derivatives (e.g., modified with an N-terminal or C-terminal protecting group).

The term "gelling" or "gelation" means a thickening of the medium that may result in a gelatinous consistency and even in a solid, rigid consistency that does not flow under its own weight.

A "gelator" is defined herein to include a non-polymeric organic compound whose molecules can establish, between themselves, at least one physical interaction leading to a self-assembly of the molecules in a carrier fluid to form a gel. The gel may result from the formation of a network of molecular nanofibers due to the stacking or aggregation of gelator molecules.

A "molecular nanofiber" is defined as a fiber with a diameter on the order of about 100 nanometers, or about 10 nanometers, or about 1 nanometer.

A "small molecule" refers to a molecule which has a molecular weight of less than about about 5000 amu, or less than 2000 amu, or less than about 1000 amu, and less than about 500 amu. A "bioactive small molecule" refers to a small molecule that has a biological activity (e.g. clinically used drugs).

"Treating" is used herein to refer to any treatment of, or prevention of, or inhibition of a disorder or disease in a subject and includes by way of example: (a) preventing the disease or disorder from occurring in a subject that may be predisposed to the disease or disorder, but has not yet been diagnosed as having it; (b) inhibiting the disease or disorder, i.e., arresting its progression; or (c) relieving or ameliorating the disease or disorder, i.e., causing regression.

The term "alkyl" means a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, and n-hexyl.

The term "alkylene" pertains to a bidentate (diradical) moiety obtained by removing two hydrogen atoms, either both from the same carbon atom, or one from each of two different carbon atoms, of a hydrocarbon compound, which may be aliphatic or alicyclic, or a combination thereof, and which may be saturated, partially unsaturated, or fully unsaturated. Examples of linear saturated $C_{1-10}$alkylene groups include, but are not limited to, —$(CH_2)_n$— where n is an integer from 1 to 10, for example, —$CH_2$— (methylene), —$CH_2CH_2$— (ethylene), —$CH_2CH_2CH_2$— (propylene), —$CH_2CH_2CH_2CH_2$— (butylene), —$CH_2CH_2CH_2CH_2CH_2$— (pentylene) and —$CH_2CH_2CH_2CH_2CH_2CH_2$— (hexylene). Examples of branched saturated $C_{1-10}$alkylene groups include, but are not limited to, —$CH(CH_3)$—, —$CH(CH_3)CH_2$—, —$CH(CH_3)CH_2CH_2$—, —$CH(CH_3)CH_2CH_2CH_2$—, —$CH_2CH(CH_3)CH_2$—, —$CH_2CH(CH_3)CH_2CH_2$—, —$CH(CH_2CH_3)$—, —$CH(CH_2CH_3)CH_2$—, and —$CH_2CH(CH_2CH_3)CH_2$—. Examples of linear partially unsaturated $C_{1-10}$alkylene groups include, but are not limited to, —CH=CH— (vinylene), —CH=CH—$CH_2$—, —CH=CH—$CH_2$—$CH_2$—, —CH=CH—$CH_2$—$CH_2$—$CH_2$—, —CH=CH—CH=CH—, —CH=CH—CH=CH—$CH_2$—, —CH=CH—CH=CH—$CH_2$—$CH_2$—, —CH=CH—$CH_2$—CH=CH—, and —CH=CH—$CH_2$—$CH_2$—CH=CH—. Examples of branched partially unsaturated $C_{1-10}$alkylene groups include, but are not limited to, —$C(CH_3)$=CH—, —$C(CH_3)$=CH—$CH_2$—, and —CH=CH—$CH(CH_3)$—. Examples of alicyclic saturated $C_{1-10}$alkylene groups include, but are not limited to, cyclopentylene (e.g., cyclopent-1,3-ylene), and cyclohexylene (e.g., cyclohex-1,4-ylene). Examples of alicyclic partially unsaturated $C_{1-10}$alkylene groups include, but are not limited to, cyclopentenylene (e.g., 4-cyclopenten-1,3-ylene), and cyclohexenylene (e.g., 2-cyclohexen-1,4-ylene, 3-cyclohexen-1,2-ylene, and 2,5-cyclohexadien-1,4-ylene).

The term "aryl," as used herein, means a phenyl group or a naphthyl group. The aryl groups of the present invention can be optionally substituted with one, two, three, four, or five substituents independently selected from the group consisting of alkenyl, alkoxy, alkoxycarbonyl, alkoxysulfonyl, alkyl, alkylcarbonyl, alkylcarbonyloxy, alkylsulfonyl, alkylthio, alkynyl, amido, amino, carboxy, cyano, formyl, halo, haloalkoxy, haloalkyl, hydroxyl, hydroxyalkyl, mercapto, nitro, silyl and silyloxy.

The term "arylalkyl" or "aralkyl" as used herein, means an aryl group, as defined herein, appended to the parent molecular moiety through an alkyl group, as defined herein. Representative examples of arylalkyl include, but are not limited to, benzyl, 2-phenylethyl, 3-phenylpropyl, and 2-naphth-2-yl-ethyl.

The term "heteroaryl" as used herein, include aromatic ring systems, including, but not limited to, monocyclic, bicyclic and tricyclic rings, and have 3 to 12 atoms including at least one heteroatom, such as nitrogen, oxygen, or sulfur. For purposes of exemplification, which should not be construed as limiting the scope of this invention: azaindolyl, benzo(b)thienyl, benzimidazolyl, benzofuranyl, benzoxazolyl, benzothiazolyl, benzothiadiazolyl, benzotriazolyl, benzoxadiazolyl, furanyl, imidazolyl, imidazopyridinyl, indolyl, indolinyl, indazolyl, isoindolinyl, isoxazolyl, isothiazolyl, isoquinolinyl, oxadiazolyl, oxazolyl, purinyl, pyranyl, pyrazinyl, pyrazolyl, pyridinyl, pyrimidinyl, pyrrolyl, pyrrolo[2,3-d]pyrimidinyl, pyrazolo[3,4-d]pyrimidinyl, quinolinyl, quinazolinyl, triazolyl, thiazolyl, thiophenyl, tetrahydroindolyl, tetrazolyl, thiadiazolyl, thienyl, thiomorpholinyl, triazolyl or tropanyl. The heteroaryl groups of the invention are substituted with 0, 1, 2, or 3 substituents independently selected from alkenyl, alkoxy, alkoxycarbonyl, alkoxysulfonyl, alkyl, alkylcarbonyl, alkylcarbonyloxy, alkylsulfonyl, alkylthio, alkynyl, amido, amino, carboxy, cyano, formyl, halo, haloalkoxy, haloalkyl, hydroxyl, hydroxyalkyl, mercapto, nitro, silyl and silyloxy.

The term "heteroarylalkyl" or "heteroaralkyl" as used herein, means a heteroaryl, as defined herein, appended to the parent molecular moiety through an alkyl group, as defined herein. Representative examples of heteroarylalkyl include, but are not limited to, pyridin-3-ylmethyl and 2-(thien-2-yl)ethyl.

EXEMPLIFICATION

The invention will be more readily understood by reference to the following examples, which are included merely for purposes of illustration of certain aspects and embodiments of the present invention, and are not intended to limit the invention.

Example 1

Synthesis of a Paclitaxel-Containing Precursor

[A] Synthesis of 2: Paclitaxel (1, 170.6 mg, 0.2 mmol) was added to succinic anhydride (70 mg, 0.7 mmol) in the presence of 4-dimethylamino-pyridine (41 mg, 0.33 mmol) which was previously dried under vacuum for 2 h. Then, 5 mL of dry pyridine were added and the solution was stirred for 3 h at room temperature. Dosio, F.; Brusa, P.; Crosasso, P.; Arpicco, S.; Cattel, L. *J. Control. Rel.* 1997, 47, 293-304.

The 2'-succinyl-paclitaxel (2) was purified by extraction according to following procedure: After 20 mL of dry dichloromethane (DCM) were added into the reaction mixture, the organic phase was washed using 1 M HCl solution (20 mL×3) and water (20 mL×3). Water phase was extracted by DCM (10 mL×3). The organic phase was combined and washed by brine (10 mL×3) and dried over $Na_2SO_4$. The filtrate was concentrated on rotary evaporator and the crude product was used without further purification.

[B] Synthesis of 3: Compound 2 (190.6 mg, 0.2 mmol) was mixed with N-hydroxysuccinimide (23.0 mg, 0.2 mmol); then, 10 mL of $CHCl_3$ were added to obtain a well-dispersed solution. After N,N'-Dicylcohexylcarbodiimide (41.2 mg, 0.2 mmol) was added into the mixture, the solution was stirred for 4 h at room temperature. The 2'-NHS-succinyl-paclitaxel (3) was purified by chromatography with chloroform-methanol as the eluent (19:1).

[C] Synthesis of 5a: Compound 4 (48.6 mg, 0.057 mmol) was dissolved in 5 mL of water, and the pH of the solution was adjusted to 8.5 with sodium carbonate. Compound 3 (50 mg, 0.0476 mmol) was dissolved in 3 mL of acetone, and then added into the water solution dropwise. The ratio of water/acetone was adjusted to keep the reaction mixture clear. The mixture was stirred at room temperature for 12 h. The reaction mixture was subjected to HPLC purification. Compound 5a was purified with water-methanol eluent (from 7:3 to 1:9).

Example 2

Drug Release

The experimental procedure used to determine drug release was as follows. To the solution of 0.25 mL of water containing 2 mg of 5a at pH of about 7.3, alkaline phosphatase (5 U, 1 μL) was added to form the sample 'Gel 5b' in FIG. 3B. 0.25 mL of fresh PBS buffer solution (100 mM) were added onto the top of the gel. At the end of every hour, the PBS buffer was taken out for analysis, and another 0.25-mL aliquot of fresh PBS buffer (100 mM) was added onto the top of the hydrogel.

To the solution of 0.5 mL of water containing 3 mg of 4 and 3 mg of 5a at pH=7.3, alkaline phosphatase (5 U, 1 μL) was added to form the sample 'mixed gel' in FIG. 3B. 0.5 mL of fresh PBS buffer solution (100 mM) were added onto the top of the gel. At the end of every hour, the PBS buffer was taken out for analysis, and another 0.5-mL aliquot of fresh PBS buffer (100 mM) was added onto the hydrogels.

The samples of the PBS solutions that were taken out by HPLC were analyzed, and Table 1 (below) shows the result of the analysis. (The integration of 0.56 mg of 5b (standard) is 20761595 μV*sec. The detection wavelength is 220 nm.) The data suggest that the release of 5b was almost linear at a rate of 0.05%/hr in 'Gel 5b' and 0.016%/hr in 'mixed gel'.

TABLE 1

Raw Data of Drug Release Experiment.

| Integration (μV*sec) | Gel 5b (0.8%) 0.25 mL | Mixed gel (0.6%) 0.50 mL |
|---|---|---|
| 1st hour | 37169 | 24557 |
| 2nd hour | 35007 | 27374 |
| 3rd hour | 39544 | 20095 |
| 4th hour | 50529 | 28723 |
| 5th hour | 51411 | 17938 |
| 6th hour | 41218 | 12641 |

Example 3

Cytotoxicity Measurements

Figure 4:
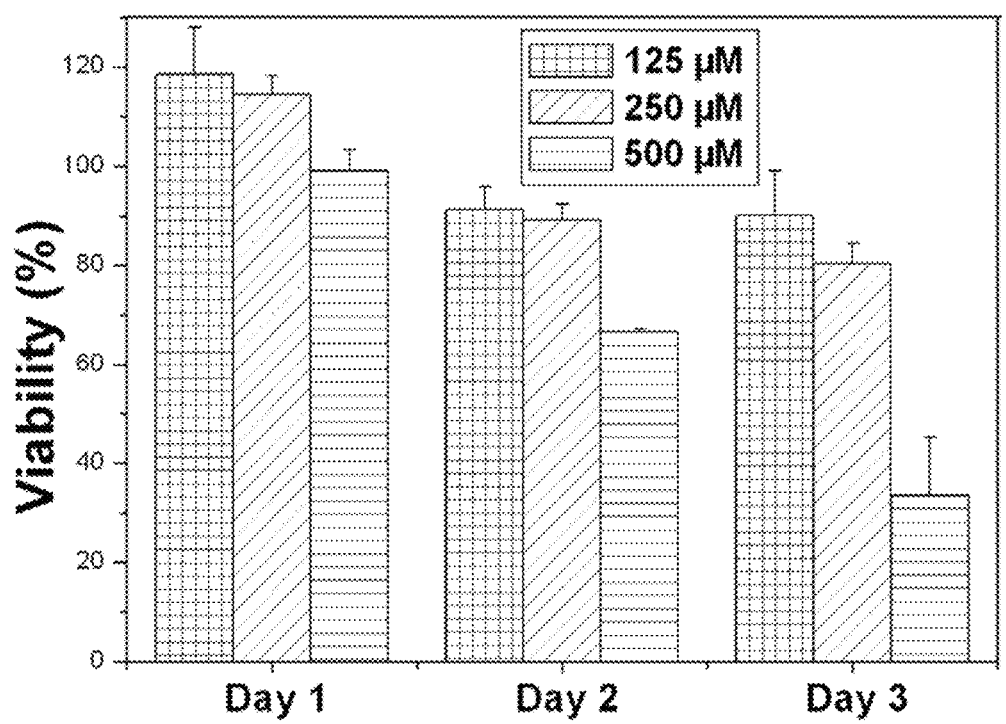
FIG. 4 depicts the cytotoxicity of 4 against HeLa cell.
Figure 5:
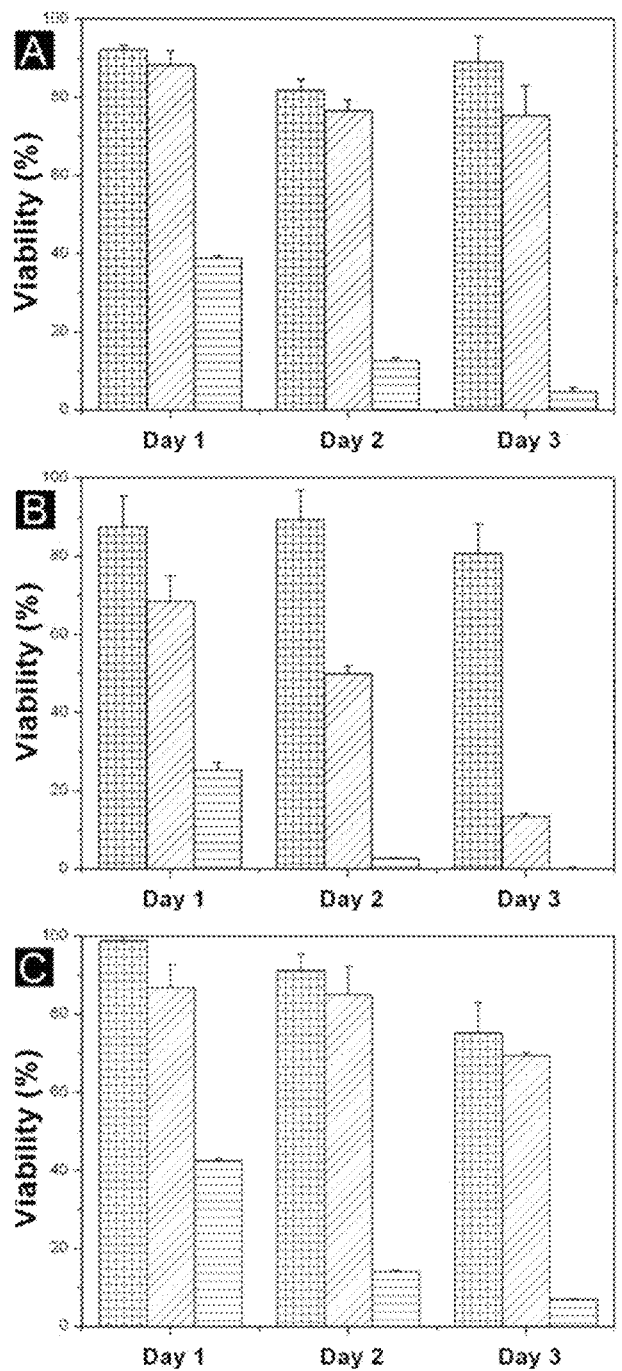
FIG. 5 depicts the cytotoxicity test of (A) 1, (B) 5a and (C) 5b against HeLa cell.
Figure 6:
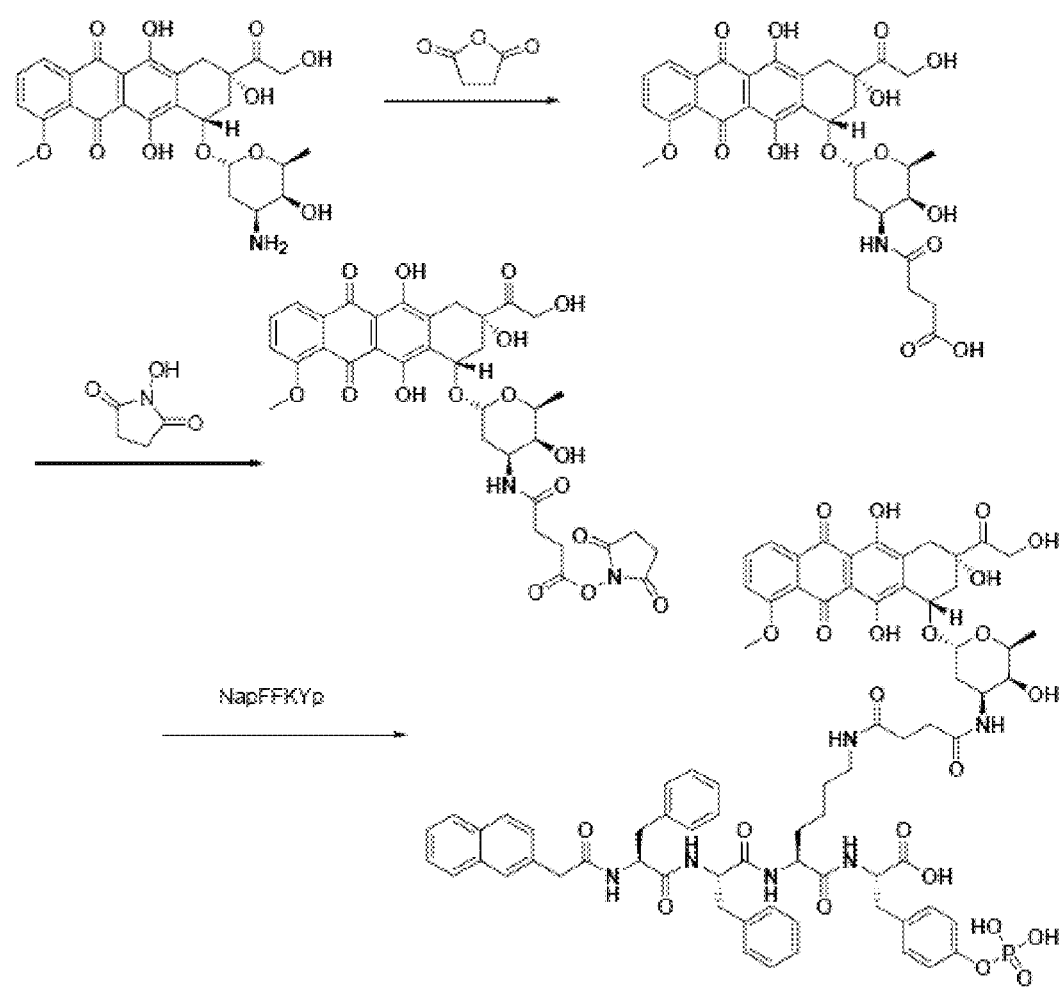
FIG. 6 depicts an example of the synthesis of a doxorubicin-containing precursor. Daunorubicin-containing precursors can be made using the same approach.

FIG. 4 depicts the cytotoxicity of 4 against HeLa cells; FIG. 5 depicts the cytotoxicity test of (A) 1, (B) 5a and (C) 5b against HeLa cells. The $IC_{50}$ of 4 (at 48 h) is higher than the highest concentration (500 μM) tested. The result shows that 4 has very limited toxicity.

INCORPORATION BY REFERENCE

All of the U.S. patents and U.S. patent application publications cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by this disclosure.

We claim:

1. A compound having the following formula:

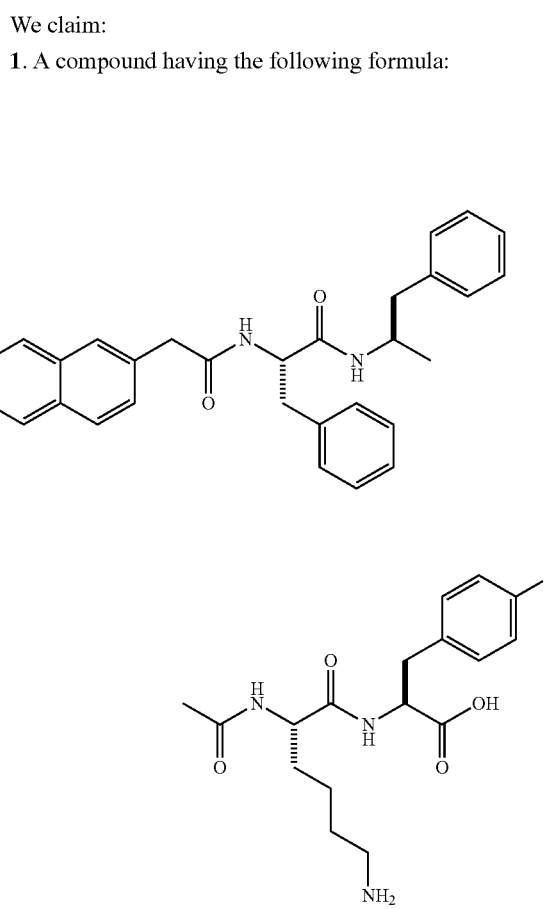

wherein,
R is —OH or —OPO$_3$H$_2$.

2. The compound of claim 1, wherein R is —OH.
3. The compound of claim 1, wherein R is —OPO$_3$H$_2$.
4. A self-assembled molecular nanofiber comprising:
a plurality of compounds of claim 1, wherein R is —OH; and
either (i) a plurality of compounds of Formula I or (ii) a plurality of compounds of Formula II:

(i)

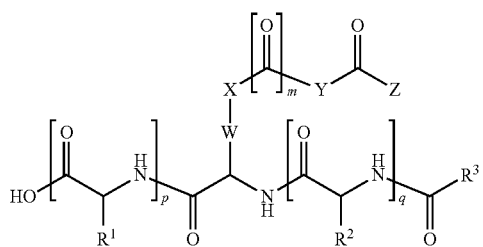

I wherein, independently for each occurrence,
R$^1$ is

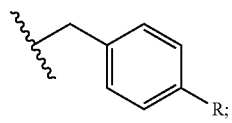

R is —H, —OH or —OPO$_3$H$_2$;
p is 0-8;
R$^2$ is

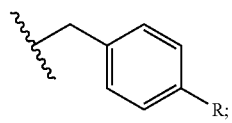

q is 0-8;
R$^3$ is aryl, aralkyl, heteroaryl, or heteroaralkyl;
W is (C$_1$-C$_{10}$)alkylene;
X is —O—, —N(H)—, —S— or —CH$_2$—;
m is 0 or 1;
Y is (C$_1$-C$_{10}$)alkylene; and
Z is a bioactive small molecule;
provided that the sum of p and q is 2, 3, 4, 5, 6, 7 or 8; and at least one instance of R is —OH or —OPO$_3$H$_2$; or (ii)

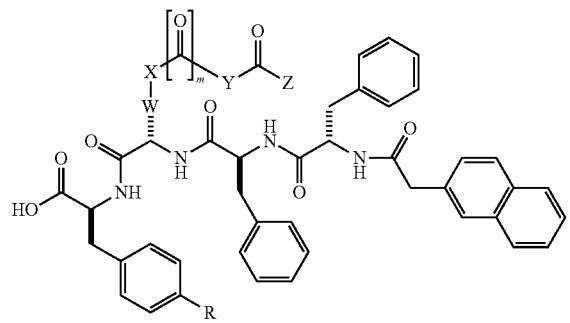

II wherein, independently for each occurrence,
R is —OH or —OPO$_3$H$_2$;
W is (C$_1$-C$_{10}$)alkylene;
X is —O—, —N(H)—, —S— or —CH$_2$—;
m is 0 or 1;
Y is (C$_1$-C$_{10}$)alkylene; and
Z is a bioactive small molecule.

5. The self-assembled molecular nanofiber of claim 4, wherein the self-assembled molecular nanofiber has a diameter of about 100 nm.
6. The self-assembled molecular nanofiber of claim 4, wherein the self-assembled molecular nanofiber has a diameter of about 10 nm.
7. The self-assembled molecular nanofiber of claim 4, wherein the self-assembled molecular nanofiber has a diameter of about 1 nm.
8. The self-assembled molecular nanofiber of claim 4, further comprising an antineoplastic agent.
9. A supramolecular hydrogel, comprising the self-assembled molecular nanofiber of claim 4; and a carrier fluid.
10. The supramolecular hydrogel of claim 9, further comprising an antineoplastic agent.
11. The self-assembled molecular nanofiber of claim 4, wherein in the compound of Formula I or Formula II Z is an antineoplastic agent.
12. A method of treating cancer, tumors, malignancies, neoplasms, or other dysproliferative diseases, comprising administering to a patient in need thereof a therapeutically effective amount of a supramolecular hydrogel comprising a carrier fluid and a plurality of self-assembled molecular nanofibers of claim 11.
13. The method of claim 12, wherein in the compounds of Formula I or Formula II R is —OPO$_3$H$_2$.
14. The method of claim 12, wherein in the compounds of Formula I or Formula II wherein R is —OH.
15. The method of claim 12, further comprising the step of administering an antineoplastic agent.
16. The method of claim 12, wherein the method is a method of treating a neoplasm.

* * * * *